US006937754B1

(12) United States Patent
Eguchi

(10) Patent No.: US 6,937,754 B1
(45) Date of Patent: Aug. 30, 2005

(54) INSPECTION EQUIPMENT

(75) Inventor: Naoya Eguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 581 days.

(21) Appl. No.: 09/588,292

(22) Filed: Jun. 7, 2000

(30) Foreign Application Priority Data

Jun. 10, 1999 (JP) .......................................... 11-164448

(51) Int. Cl.$^7$ .............................. G06K 9/00; H04N 7/18
(52) U.S. Cl. ......................... 382/145; 382/149; 348/92; 348/125; 356/237.1
(58) Field of Search ................................ 382/141–152; 348/96–92, 125–134; 250/223 R, 223 B; 356/237.1–237.6

(56) References Cited

U.S. PATENT DOCUMENTS

| 4,514,858 | A | * | 4/1985 | Novak .......................... 378/34 |
| 5,479,252 | A | * | 12/1995 | Worster et al. ............. 356/237 |
| 5,619,429 | A | * | 4/1997 | Aloni et al. ................. 364/552 |
| 5,638,206 | A | * | 6/1997 | Sumiya et al. .............. 359/368 |
| 5,761,336 | A | * | 6/1998 | Xu et al. ..................... 382/141 |
| 5,774,222 | A | * | 6/1998 | Maeda et al. ............... 356/394 |
| 5,912,735 | A | * | 6/1999 | Xu ............................. 356/450 |
| 6,388,744 | B1 | * | 5/2002 | Kubota et al. ........... 356/237.3 |

FOREIGN PATENT DOCUMENTS

EP           0 582 884      *    2/1994

OTHER PUBLICATIONS

Liu et al. "All–Solid–State Tunable Ultraviolet Ce Activated Flouride Laser Systems Directly Pumped by the Fourth and Fifth Harmonic of Nd: YAG Lasers" 1998. IEEE. pp. 343–345.*
E. Wagner et al. (Eds), Sensors, vol. 6, p. 137, VCH, Weinheim, Germany, 1992.

* cited by examiner

Primary Examiner—Bhavesh M. Mehta
Assistant Examiner—Aaron Carter
(74) Attorney, Agent, or Firm—Sonnenschein, Nath & Rosenthal LLP

(57) ABSTRACT

To inspect a finer device pattern formed in a semiconductor wafer, there is provided an inspection equipment including means for supporting a semiconductor wafer as a specimen and moving it to a predetermined position of inspection, means for projecting an ultraviolet light onto the specimen supported on the specimen supporting means, an ultraviolet imaging means for detecting a reflected light or transmitted light from the specimen illuminated by the ultraviolet light projecting means and picking up an image of the specimen, means for processing the image picked up by the ultraviolet imaging means. The image picked up by the imaging means is processed and analyzed by the image processing means to inspect the specimen.

15 Claims, 12 Drawing Sheets

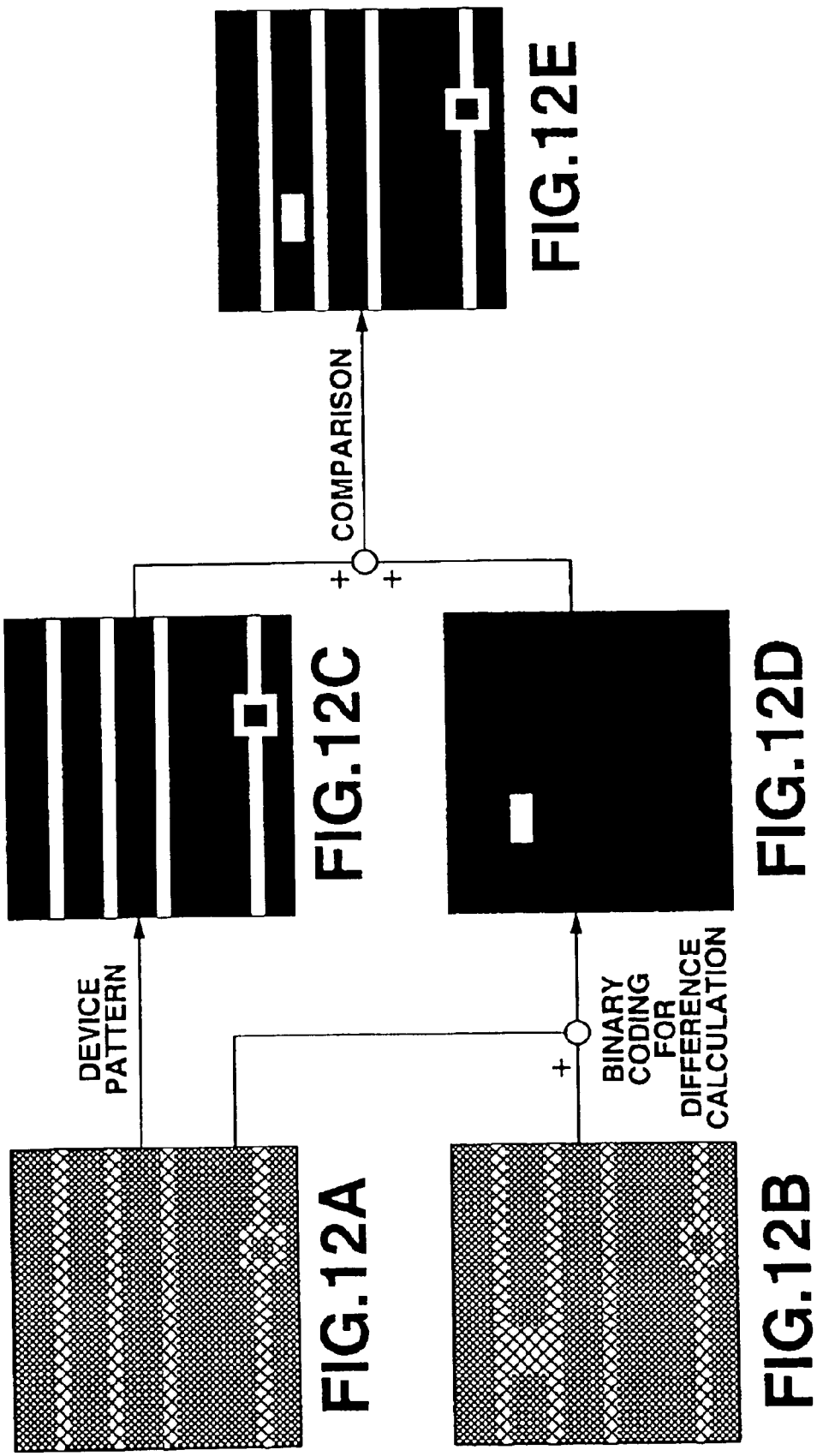

INSPECTION EQUIPMENT

RELATED APPLICATION DATA

The present application claims priority to Japanese Application No. P11-164448 filed Jun. 10, 1999, which application is incorporated herein by reference to the extent permitted by law.

BACKGROUND OF THE INVENTION

1. Field of the Invention

The present invention relates to an inspection equipment used to inspect a semiconductor wafer having a predetermined device pattern formed therein, and the like.

2. Description of the Related Art

A semiconductor device is produced with a fine device pattern formed on a semiconductor wafer. In forming such a device pattern, dust or scratch on the semiconductor wafer surface will cause a defect. The semiconductor incurring such a defect is rejected as an unacceptable device, which will lower the yield at the semiconductor device production line.

Accordingly, to stabilize the yield of the production line at a high level, it is necessary to early find a defect caused by dust or scratch, locate the cause of the defect, and apply effective remedies to the manufacturing equipment and process.

If any of the produced semiconductor devices is found defective, an inspection equipment is used to examine what the defect is and classify the defect, and find out where in the manufacturing equipment and process the cause of the defect exists. What the defect is has been examined by an inspection equipment like an optical microscope. For identification, a defect is observed by magnifying its image.

Along with a higher degree of integration in a semiconductor device, a finer and finer device pattern has been demanded. Recently, a line width of less than 0.18 μm has been attained. Thus, the defect size has become so fine that it has become difficult for the conventional inspection equipment to examine what the defect is and classify the detect.

OBJECT AND SUMMARY OF THE INVENTION

It is therefore an object of the present invention to overcome the above-mentioned drawbacks of the prior art by providing an inspection equipment capable of inspecting a fine device pattern.

The above object can be attained by providing an inspection equipment including according to the present invention:

means for supporting a specimen and moving it to a predetermined position of inspection;

means for projecting an ultraviolet light onto the specimen supported on the specimen supporting means;

an ultraviolet imaging means for detecting a reflected light or transmitted light from the specimen illuminated by the ultraviolet light projecting means and picking up an image of the specimen; and means for processing the image picked up by the ultraviolet imaging means;

the image picked up by the ultraviolet imaging means being processed and analyzed by the image processing means to inspect the specimen.

With the inspection equipment according to the present invention, using an ultraviolet light having a very short wavelength to image a specimen, it is possible to inspect a finer device pattern than the conventional inspection using a visible light can inspect.

These objects and other objects, features and advantages of the present intention will become more apparent from the following detailed description of the preferred embodiments of the present invention when taken in conjunction with the accompanying drawings.

BRIEF DESCRIPTION OF THE DRAWINGS

FIGS. 12a–12e explains a method of detecting a defect based on a reference image and defect image.

DETAILED DESCRIPTION OF THE PREFERRED EMBODIMENTS

Figure 1:
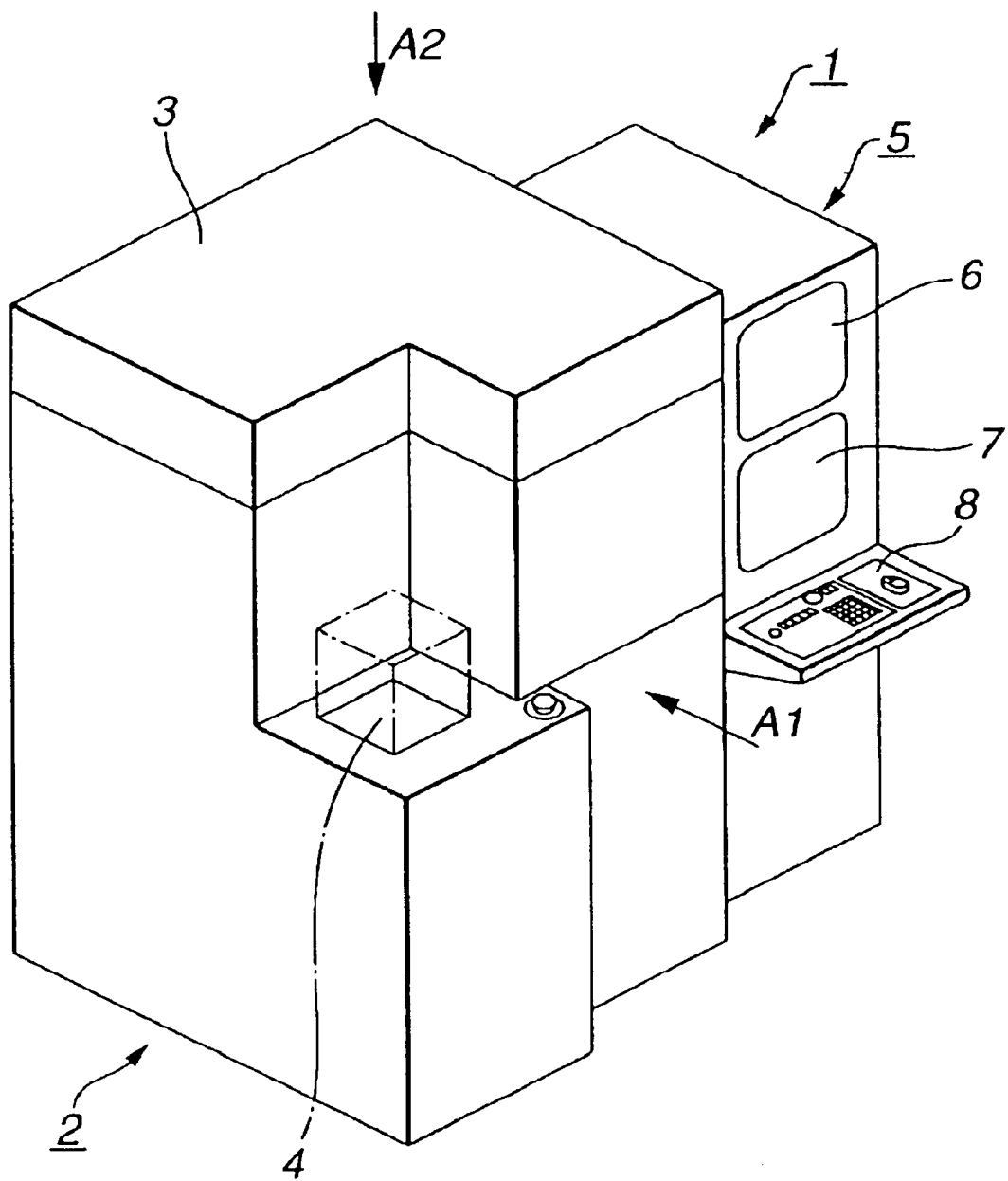
FIG. 1 is an external view of the inspection equipment according to the present invention.

Referring now to FIG. 1, there is given an external view of the inspection equipment according to the present invention. The inspection equipment is generally indicated with a reference 1. This inspection equipment is intended for inspection of a semiconductor wafer having a predetermined device pattern formed thereon. When a defect is found in the semiconductor wafer having the predetermined device pattern formed therein, the inspection equipment is used to examine what the defect is and classify the defect.

As shown in FIG. 1, the inspection equipment 1 includes a dedusting clean unit 2 to keep clean the internal environment in the inspection equipment. The clean unit 2 has provided atop thereof a clean air unit 3 to supply clean air from which dust has been removed. With the dust-free clean air supplied from the clean air unit 3, the air cleanliness in the internal environment can be kept at the Class I or so.

In the clean unit 2 of the inspection equipment 1, a semiconductor wafer having a predetermined device pattern formed therein is inspected. The semiconductor wafer as a specimen to be inspected is put into a predetermined closable container 4 which will be transferred into the clean unit 2. For inspection of the semiconductor wafer, the container 4 having the semiconductor wafer placed therein is installed to the clean unit as indicated with a dashed line in FIG. 1, and the semiconductor wafer is taken out of the container 4 by a transfer robot which will further be described later and placed on an inspection stage disposed inside the clean unit 2, so as not to be in contact with the atmosphere.

Since the semiconductor wafer is thus inspected inside the clean unit 2, it is possible to keep dust off the semiconductor wafer under inspection. Also, since the semiconductor wafer as a specimen is put in the closable container 4 and transferred while being placed in the container 4 into the clean unit 2, it is possible to keep dust off the semiconductor wafer even with no high air cleanliness of the entire environment in which the inspection equipment 1 is installed, as long as only the inside of the clean unit 2 and that of the container 4 are kept clean at a sufficient level.

By limiting a space in which the air cleanliness should be high for the actual inspection, it is possible to attain a high air cleanliness and considerably reduce the costs for realizing a clean environment. For a mechanical interface between the closable container 4 and clean unit 2, a so-called standard mechanical interface (SMIF) is preferably usable. In this case, a so-called SMIF pod is used for the closable container 4.

Also, the inspection equipment 1 is provided outside the clean unit 2 with an external unit 5 in which a computer for controlling the inspection equipment 1 is disposed. The external unit 5 has also disposed therein a display unit 6 to display images of a semiconductor wafer having been inspected, and a display unit 7 to display testing conditions. Further the external unit 5 is provided outside thereof with an input unit 8 for supplying instructions, etc. to the inspection equipment 1. For inspecting a semiconductor wafer by the inspection equipment 1, the inspector supplies necessary instructions to the inspection equipment 1 from the input unit 8 disposed outside the external unit 5 while watching the display units 6 and 7 provided in the external unit 5.

Figure 2:
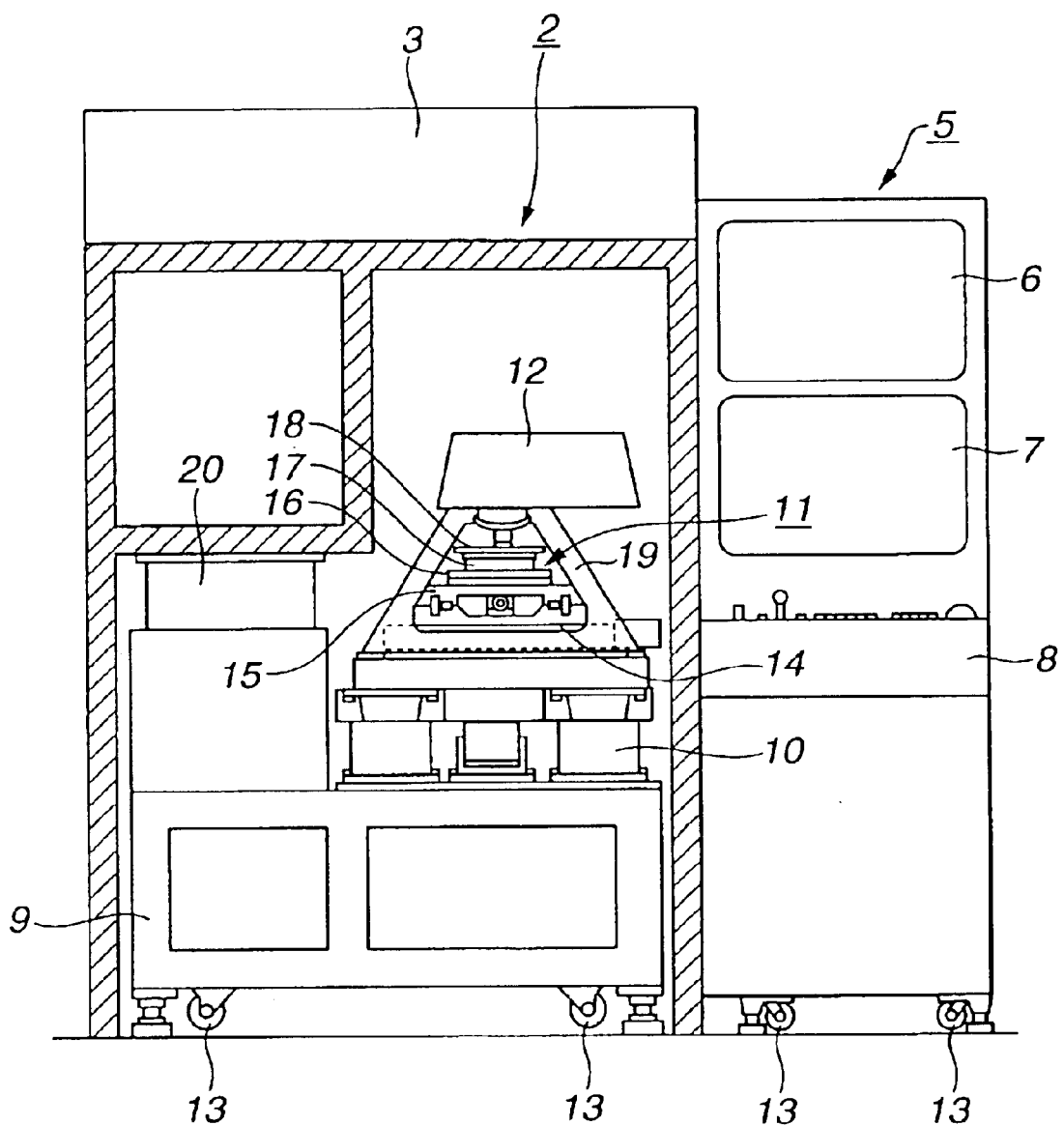
FIG. 2 is a front view of the inspection equipment in FIG. 1, from the direction of arrow A1 in FIG. 1, showing the internal structure of a clean unit in the inspection equipment.
Figure 3:
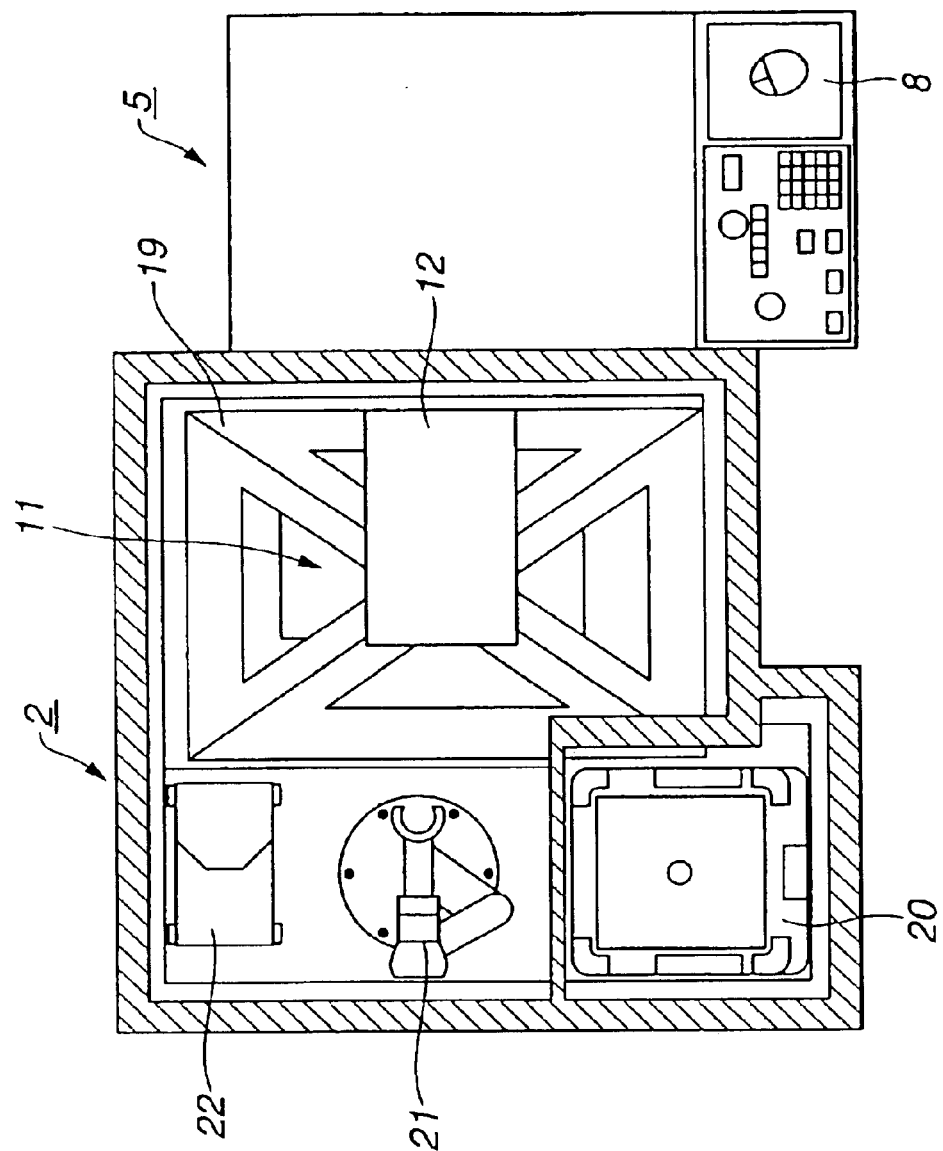
FIG. 3 is a plan view of the inspection equipment in FIG. 1, from the direction of arrow A2 in FIG. 1, showing the internal structure of the clean unit in the inspection equipment.

The inside of the clean unit 2 of the inspection equipment 1 will be described hereinbelow with reference to FIGS. 2 and 3. FIG. 2 is a front view of the inspection equipment 1 in FIG. 1, from the direction of arrow A1 in FIG. 1, showing the internal structure of the clean unit 2 in the inspection equipment 1, and FIG. 3 is a plan view of the inspection equipment 1 in FIG. 1, from the direction of arrow A2 in FIG. 1, showing the internal structure of the clean unit 2 in the inspection equipment 1.

As shown in FIG. 2, there are provided inside the clean unit 2 a support pedestal 9, vibration controller 10 mounted on the support pedestal 9, inspection stage 11 mounted on the vibration controller 10, and an optical unit 12 mounted on the vibration controller 10.

The support pedestal 9 support other component units provided inside the clean unit 2. The support pedestal 9 and external unit 5 are provided at the bottom thereof with their respective wheels 13, so that the inspection equipment 1 can easily be relocated. Also, the support pedestal 9 and external unit 5 are provided at the bottom thereof with their respect fixing legs. To fix the inspection equipment 1 on the floor, the fixing legs are placed on the floor surface while the wheels 13 are off the floor surface, as shown in FIG. 2.

The vibration controller 10 is provided to control a vibration transmitted from the floor or a one taking place when the inspection stage 11 is moved. Since the inspection equipment 1 is used to inspect a semiconductor wafer having a fine device pattern formed therein, even a slight vibration will adversely affect the inspection. To avoid this, the vibration controller 10 of the inspection equipment 1 functions to control the vibration.

For this inspection equipment 1, the vibration controller 10 should preferably be a so-called active vibration controller designed to move, upon detection of a vibration, in a direction of canceling the vibration. Thus, this type of vibration controller can eliminate the vibration quickly and effectively.

Since the inspection equipment 1 inspects a semiconductor wafer having a fine device pattern formed therein with a high resolution using an ultraviolet light, the inspection is susceptible to a vibration. Using the active vibration controller having an excellent vibration control function as the vibration controller 10 for the inspection equipment 1, the influence of a vibration can effectively be controlled, so that the inspection equipment 1 can show an improved performance in inspection of a semiconductor wafer with a high resolution using an ultraviolet light.

The inspection stage 11 mounted on the vibration controller 10 supports a semiconductor wafer as a specimen. The inspection stage 11 supports the specimen and also moves it to a predetermined inspection position.

More specifically, the inspection stage 11 includes an X stage 14 mounted on the vibration controller 10, Y stage 14 mounted on the X stage 14, θ stage 16 mounted on the Y stage 15, Z stage 17 mounted on the θ stage 16, and a suction plate 18 mounted on the Z stage 17.

The X and Y stages 14 and 15 are movable horizontally in directions, respectively, perpendicular to each other. A semiconductor wafer under inspection will be carried on the X and Y stages 14 and 15 to an inspection position.

The θ stage 16 is a so-called rotary stage to rotate a semiconductor wafer. A semiconductor wafer under inspection is rotated on the θ stage 16 so that the image of a device pattern formed on the semiconductor wafer will be in a horizontal or vertical position on the screen of the display unit.

The Z stage 17 is movable vertically to adjust the stage height. The stage height is adjusted by the Z stage 17 so that a to be checked surface of a semiconductor wafer under inspection comes to an appropriate height.

The suction plate 18 sucks a semiconductor wafer under inspection to fix the latter. A semiconductor wafer under inspection is placed on this suction plate 18, and sucked by the latter to be immovable.

Further, there is provided on the vibration controller 10 an optical unit 12 supported on a support member 19 to be positioned on the inspection stage 11. The optical unit 12 is provided to pick up the image of a semiconductor wafer under inspection. This optical unit 12 has a function to pick up the image of a semiconductor wafer under inspection with a low resolution using a visible light, and also a function to pick up the image of the semiconductor wafer with a high resolution using an ultraviolet light.

Moreover, there is provided inside the clean unit 2 an elevator 20 mounted on the support pedestal 9 as shown in FIGS. 2 and 3, and a transfer robot 21 and aligner 22 both mounted on the support pedestal 9 as shown in FIG. 3.

When semiconductor wafers are carried in the closable container 4 such as an SMIF pod to a predetermined position, the elevator 20, transfer robot 21 and aligner 22 work together to take out the semiconductor wafers from the container 4 and place it on the inspection stage 11.

More particularly, for inspection of semiconductor wafers, first the specimens are put into the closable container 4 and the container 4 is installed to the clean unit 2 as indicated with the dashed line in FIG. 1. Then, the semiconductor wafers are removed by the elevator 20 from the bottom of the container 4 in such a manner that the atmosphere will not enter into the clean unit 2. Note that semiconductor wafers as specimens are enclosed each in a magazine and the magazines each containing a semiconductor wafer is put into the closable container 4, and the elevator 20 takes out the magazines each containing the semiconductor wafer from the container 4 and lowers them.

Further, a one to be inspected is selected from the semiconductor wafers in the magazines taken out from the container 4 and lowered by the elevator 20, and it is taken out of the magazine by the transfer robot 21. The transfer robot 21 has a suction pad provided at the free end thereof. The semiconductor wafer is sucked by the suction pad and can be carried by the transfer robot 21.

The semiconductor wafer taken out by the transfer robot 21 from the magazine is carried to the aligner 22. The aligner 22 positions and centers the semiconductor wafer with reference to an orientation flat and notch pre-formed in the semiconductor wafer. The semiconductor wafer thus positioned and centered is sucked by the transfer robot 21 and carried to the inspection stage 11, and set on the suction plate 18 of the inspection stage 11.

In the above description, the mechanism to take out the semiconductor wafers from the closable container 4 having been carried to the mechanism and place a semiconductor wafer selected for inspection on the inspection stage 11 is composed of the elevator 20, transfer robot 21 and aligner 22. However, this is just a non-limitative example. This mechanism is not limited to the example alone. The mechanism may be any one which could take out semiconductor wafers from the closable container 4 and place a selected one of the semiconductor wafers on the inspection stage 11 in such a manner that the semiconductor wafer will not be exposed to the atmosphere.

Next, the inspection equipment 1 will be described in further detail herebelow with reference to FIG. 4.

Figure 4:
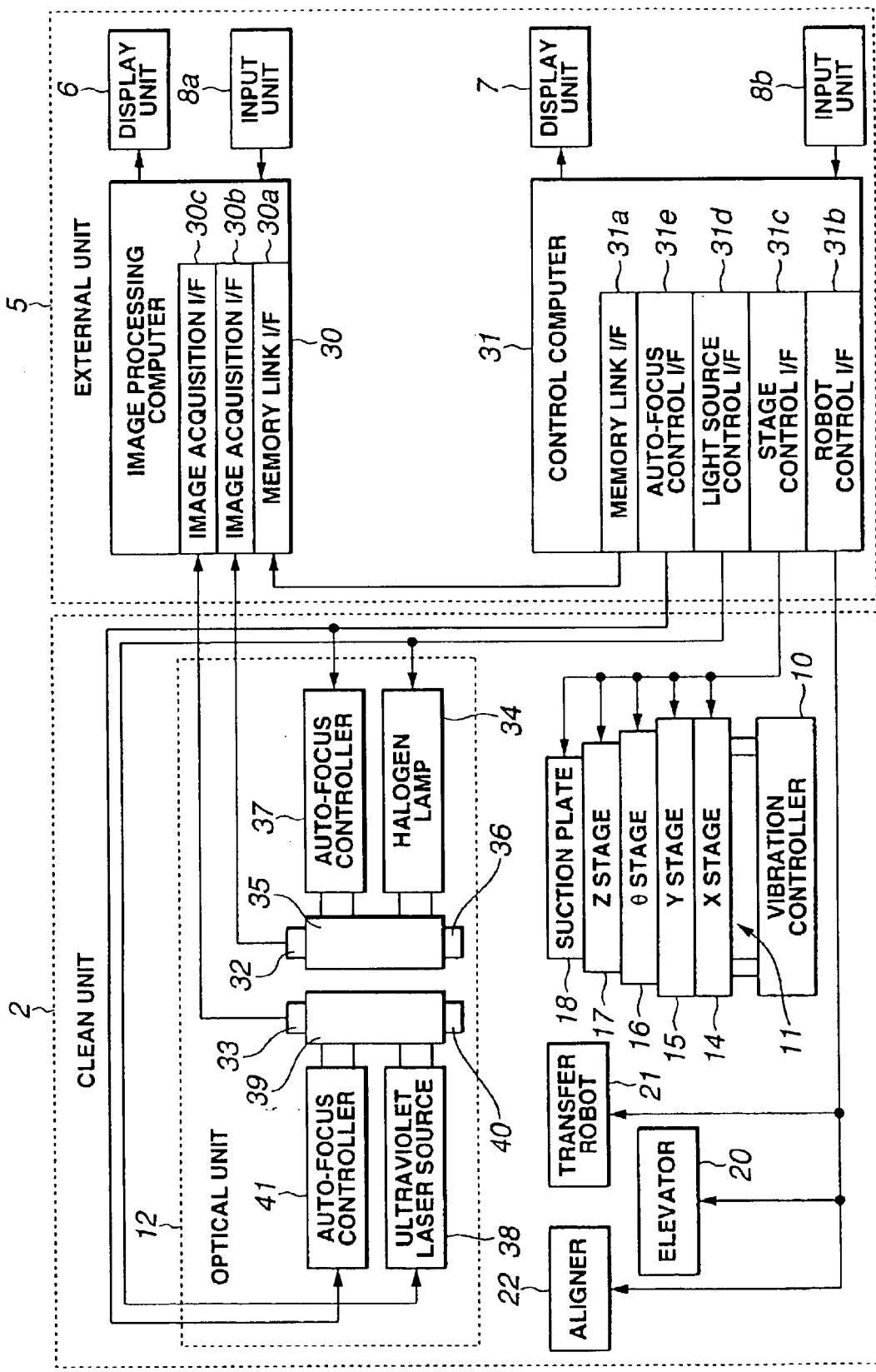
FIG. 4 is a block diagram of the inspection equipment in FIG. 1.

As shown in FIG. 4, the external unit 5 of the inspection equipment 1 incorporates an image processing computer 30 to which the display unit 6 and input unit 8a are connected, and a control computer 31 to which the display unit 7 and input unit 8b are connected. The input unit 8a connected to the image processing computer 30 and the input unit 8b connected to the control computer 31, are included in the input unit 8 shown in FIGS. 1 and 2.

When inspecting a semiconductor wafer, the image processing computer 30 is used to process an image of the semiconductor wafer, picked up by a CCD (charge-coupled device) cameras 32 and 33 provided in the optical unit 12. Namely, in the inspection equipment 1, an image of a semiconductor wafer, picked up by the CCD cameras 32 and 33 in the optical unit 12 is processed and analyzed by the image processing computer 30 to inspect the semiconductor wafer.

The input unit 8a connected to the image processing computer 30 is provided to supply the image processing computer 30 with necessary instructions for analysis of images supplied from the CCD cameras 32 and 33. The input unit 8a is a pointing device like a mouse or a keyboard for example. The display unit 6 connected to the image processing computer 30 is provided to display results of analysis of the images supplied from the CCD cameras 32 and 33. The display unit 6 is a CRT display or a liquid crystal display (LCD) for example.

For inspection of a semiconductor wafer, the control computer 31 controls the inspection stage 11, elevator 20, transfer robot 21 and aligner 22, and components provided in the optical unit 12. More specifically, in the inspection equipment 1, the inspection stage 11, elevator 20, transfer robot 21 and aligner 22, and components provided in the optical unit 12 are controlled by the control computer 31 in such a manner that for inspection of the semiconductor wafer, the image of the semiconductor wafer can correctly be imaged by the CCD cameras 32 and 33 disposed in the optical unit 12.

The input unit 8b connected to the control computer 31 is provided to supply the control computer 31 with necessary instructions for control of the inspection stage 11, elevator 20, transfer robot 21 and aligner 22, and components provided in the optical unit 12. The input unit 8b is a pointing device like a mouse or a keyboard for example. The display unit 7 connected to the control computer 31 displays various parameters for inspection of a semiconductor wafer, and it is a CRT display or a liquid crystal display (LCD) for example.

The image processing computer 30 and control computer 31 can transfer data between them via a memory link mechanism. That is, the image processing computer 30 and control computer 31 are connected to each other via memory link interfaces 30a and 31a provided for them respectively. Thus, data can be transferred between the image processing computer 30 and control computer 31.

As previously described, there are provided inside the clean unit 2 of the inspection equipment 1 the elevator 20, transfer robot 21 and aligner 22 included each as a part of a specimen place mechanism for taking out a specimen having been carried in the closable container 4, from the container 4 and place it on the inspection stage 11. These elevator 20, transfer robot 21 and aligner 22 are connected to the control computer 31 provided in the external unit 5 via a robot control interface 31b via which control signals from the control computer 31 will be sent to the elevator 20, transfer robot 21 and aligner 22, respectively, via the robot control interface 31b.

For taking out a semiconductor wafer from the container 4 having been carried and placing it on the inspection stage 11, the control computer 31 sends control signals to the elevator 20, transfer robot 21 and aligner 22 via the robot control interface 31b. Based on these control signals, the elevator 20, transfer robot 21 and aligner 22 are moved to take out the semiconductor wafer from the closable container 4 having been carried and place it on the inspection stage 11.

Also the vibration controller 10 is provided inside the clean unit 2 of the inspection equipment 1. There is provided on the vibration controller 10 the inspection stage 11 including the X stage 14, Y stage 15, θ stage 16, Z stage 17 and suction plate 18.

The X stage 14, Y stage 15, state 16, Z stage 17 and suction plate 18 are connected to the control computer 31 disposed outside the external unit 5 via the stage control interface 31c. The X stage 14, Y stage 15, θ stage 16, Z stage 17 and suction plate 18 will be supplied with control signals, respectively, from the control computer 31 via the stage control interface 31c.

For inspection of the semiconductor wafer, the control computer 31 sends control signals to the X stage 14, Y stage 15, θ stage 16, Z stage 17 and suction plate 18 respectively, via the stage control interface 31c. Based on the control signals, X stage 14, Y stage 15, θ stage 16, Z stage 17 and suction plate 18 are moved. The semiconductor wafer is fixed by the suction plate 18 which sucks the semiconductor wafer. Also the X stage 14, Y stage 15, θ stage 16 and the Z stage 17 are moved to place the semiconductor wafer at a predetermined position, angle and height.

The optical unit 12 is also provided on the vibration controller 10. For inspection of the semiconductor wafer, the optical unit 12 picks up the image of the semiconductor wafer. As having been described above, the optical unit 12 has both the functions to image the semiconductor wafer with a low resolution using a visible light and image the semiconductor with a high resolution using an ultraviolet light.

There are provided inside the optical unit 12 a mechanism for imaging the semiconductor wafer using a visible light, including a halogen lamp 34, visible light optical system 35, visible light objective lens 36, and a visible light auto-focus controller 37 in addition to the aforementioned visible light CCD camera 32.

For imaging the semiconductor wafer, the halogen lamp 34 is turned on. A drive source for the halogen lamp 34 is connected to the control computer 31 in the external unit 5 via a light source control interface 31d. The drive source for the halogen lamp 34 is supplied with a control signal from the control computer 31 via the light source control interface 31d The halogen lamp 34 is turned on and off according to the control signal.

For picking up the image of the semiconductor wafer, the halogen lamp 34 is turned on to project a visible light to the semiconductor wafer through the visible light optical system 35 and visible light objective lens 36. The image of the semiconductor wafer thus illuminated with the visible light is enlarged by the visible light objective lens 36 and the image this enlarged is picked up by the visible light CCD camera 32.

The visible light CCD camera 32 is connected to the image processing computer 30 provided in the external unit 5 via an image acquisition interface 30b. The semiconductor wafer image picked up by the visible light CCD camera 32 is acquired into the image processing computer 30 via the image acquisition interface 30b.

For imaging the semiconductor wafer with the visible light as in the above, an automatic focusing is done by the visible light auto-focus controller 37. That is, the visible light auto-focus controller 37 judges whether or not the space between the visible light objective lens 36 and semiconductor wafer coincides with the focal distance of the visible light objective lens 36. When the visible light auto-focus controller 37 judges that there is no such coincidence, it moves the visible light objective lens 36 or Z stage 17 until the to-be-inspected surface of the semiconductor wafer coincides with the focus plane of the visible light objective lens 36.

The visible light auto-focus controller 37 is connected to the control computer 31 provided in the external unit 5 via an auto-focus control interface 31e, and thus a control signal is sent to the visible light auto-focus controller 37 from the controller computer 31 via the auto-focus control interface 31e. According to the supplied control signal, the visible light auto-focus controller 37 makes an automatic focusing of the visible light objective lens 36.

There is provided inside the optical unit 12 a mechanism for imaging a semiconductor wafer using an ultraviolet light, including an ultraviolet laser source 38, ultraviolet optical system 39, ultraviolet objective lens 40 and an ultraviolet auto-focus controller 41 in addition to the aforementioned ultraviolet CCD camera 33.

For imaging the semiconductor wafer, the ultraviolet laser source 38 is turned on. A drive source for the ultraviolet laser source 38 is connected to the control computer 31 in the external unit 5 via the light source control interface 31d. The drive source for the ultraviolet laser source 38 is supplied with a control signal from the control computer 31 via the light source control interface 31d. The ultraviolet laser source 38 is turned on and off according to the control signal.

The upper limit of the wavelength of the ultraviolet solid laser practically usable in the current field of industry is 355 nm. The ultraviolet laser source 38 should preferably be able to emit an ultraviolet laser having a wavelength of less than 355 nm. It should be noted that the ultraviolet laser having the wavelength of 355 nm is provided as a third harmonic radiation of YAG laser. As will further be described later, an ultraviolet laser having a wavelength of 266 nm can be provided as a fourth harmonic radiation of YAG laser. Also, a laser whose oscillation wavelength is 166 nm has been developed. This laser may be used as the ultraviolet laser source 38. For a higher resolution, the wavelength of an ultraviolet laser emitted from the ultraviolet laser source 38 should preferably be shorter. However, if the wavelength is too short, it is difficult to build an optical system supporting the wavelength. Therefore, the wavelength λ of the ultraviolet laser emitted from the ultraviolet laser source 38 should preferably ne 355 to 166 nm.

For picking up the image of the semiconductor wafer, the ultraviolet laser source 38 is turned on to project an ultraviolet light to the semiconductor wafer through the ultraviolet optical system 39 and ultraviolet objective lens 40. The image of the semiconductor wafer thus irradiated with the ultraviolet light is enlarged by the ultraviolet objective lens 40 and the image this enlarged is picked up by the ultraviolet CCD camera 33.

The ultraviolet CCD camera 33 is connected to the image processing computer 30 provided in the external unit 5 via the image acquisition interface 30c. The semiconductor wafer image picked up by the ultraviolet CCD camera 33 is acquired into the image processing computer 30 via the image acquisition interface 30c.

For imaging the semiconductor wafer with the ultraviolet light as in the above, an automatic focusing is done by the ultraviolet auto-focus controller 41. That is, the ultraviolet auto-focus controller 41 judges whether or not the space between the ultraviolet objective lens 40 and semiconductor wafer coincides with the focal distance of the ultraviolet objective lens 40. When the ultraviolet auto-focus controller 41 judges that there is no such coincidence, it moves the ultraviolet objective lens 40 or Z stage 17 until the to-be-inspected surface of the semiconductor wafer coincides with the focus plane of the ultraviolet objective lens 40.

The ultraviolet auto-focus controller 41 is connected to the control computer 31 provided in the external unit 5 via the auto-focus control interface 31e, and thus a control signal is sent to the ultraviolet auto-focus controller 41 from the controller computer 31 via the auto-focus control interface 31e. According to the supplied control signal, the ultraviolet auto-focus controller 41 makes an automatic focusing of the ultraviolet objective lens 40.

The optical system of an optical unit 12 in the inspection equipment 1 will be described in further detail herebelow with reference to FIG. 5. Note that the auto-focus controllers 37 and 41 will be not further be described. The optical system for illuminating a semiconductor wafer under inspection and the optical system for imaging the semiconductor wafer will be described herebelow.

Figure 5:
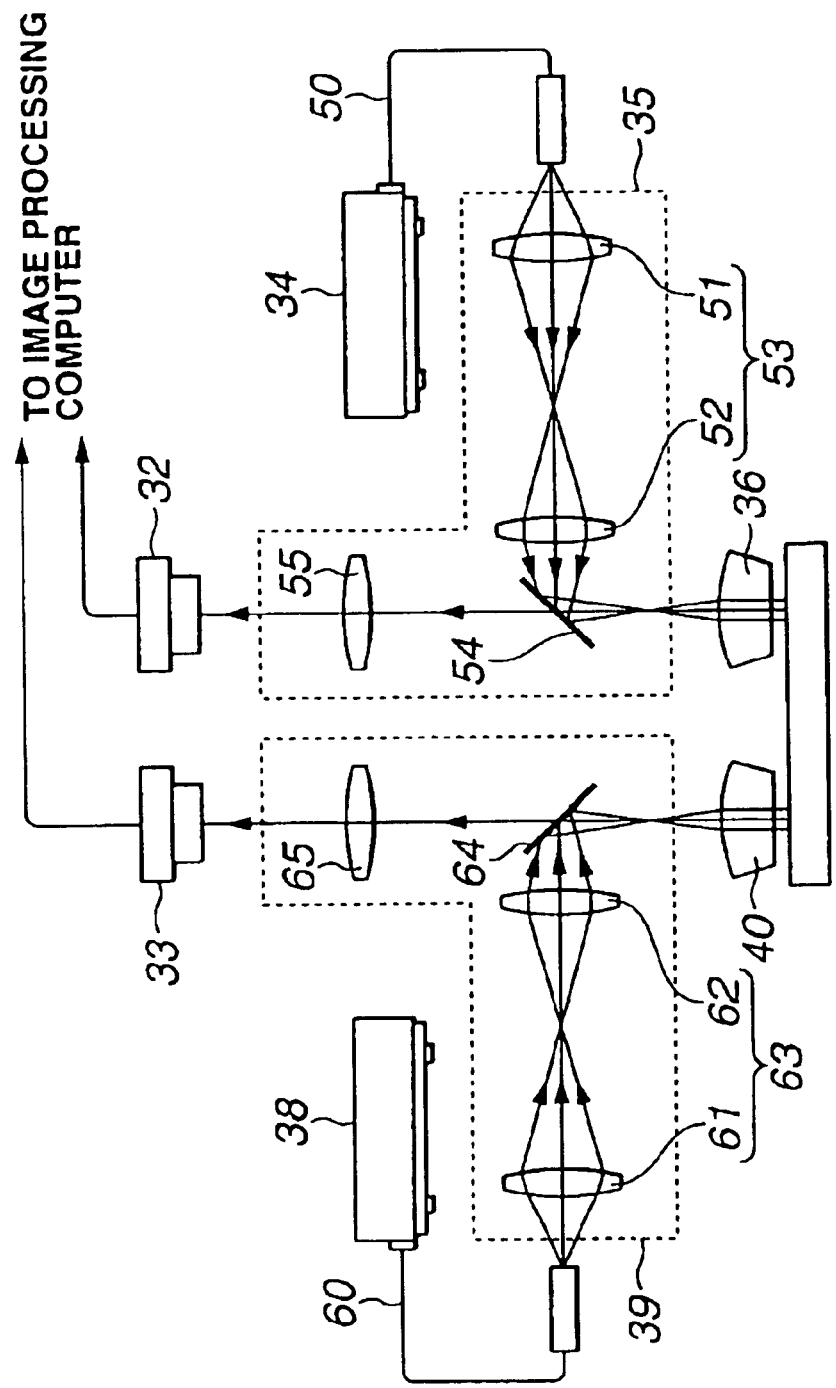
FIG. 5 shows an example of the construction of the optical system of an optical unit in the inspection equipment in FIG. 1.

As shown in FIG. 5, the optical unit 12 includes the halogen lamp 34, visible light optical system 35 and the visible light objective lens 36 as having previously been described to pick up the image of a semiconductor wafer using a visible light.

The visible light from the halogen lamp 34 is guided to the visible light optical system 35 through an optical fiber 50. The visible light optical system 35 includes an illuminating optical system 53 composed of two lenses 51 and 52. The visible light guided to the visible light optical system 35 through the optical fiber 50 is first incident upon the illuminating optical system 53. The visible light thus guided to the visible light optical system 35 through the optical fiber 50 is incident upon a half mirror 54 via the illuminating optical system 53, and reflected by the half mirror 54 towards the visible light objective lens 36. The visible light is incident upon the semiconductor wafer through the visible light objective lens 36. Thus, the semiconductor wafer is illuminated with the visible light.

The image of the semiconductor wafer illuminated with the visible light is enlarged by the visible light objective lens 36 and picked up by the visible light CCD camera 32. Namely, the reflected light from the visible light-illuminated semiconductor wafer is incident upon the visible light CCD camera 32 through the visible light objective lens 36, half mirror 54 and an imaging lens 55. Thus, the enlarged image of the semiconductor wafer is picked up by the visible light CCD camera 32. The image of the semiconductor wafer, picked up by the visible light CCD camera 32 (will be referred to as "visible image" hereinafter) is sent to the image processing computer 30.

As shown in FIG. 5, the optical unit 12 includes the ultraviolet laser source 38, ultraviolet optical system 39 and the ultraviolet objective lens 40 as having previously been described to pick up the image of a semiconductor wafer using an ultraviolet light.

The ultraviolet light from the ultraviolet laser source 38 is guided to the ultraviolet optical system 39 through an optical fiber 60. The ultraviolet optical system 39 includes an illuminating optical system 63 composed of two lenses 61 and 62. The ultraviolet light guided to the ultraviolet optical system 39 through the optical fiber 60 is first incident upon the illuminating optical system 63. The visible light thus guided to the ultraviolet optical system 39 through the optical fiber 60 is incident upon a half mirror 64 via the illuminating optical system 63, and reflected by the half mirror 64 towards the ultraviolet objective lens 40. The ultraviolet light is incident upon the semiconductor wafer through the ultraviolet objective lens 40. Thus, the semiconductor wafer is irradiated with the ultraviolet light.

The image of the semiconductor wafer irradiated with the ultraviolet light is enlarged by the ultraviolet objective lens 40 and picked up by the ultraviolet CCD camera 33. Namely, the reflected light from the ultraviolet light-irradiated semiconductor wafer is incident upon the ultraviolet light CCD camera 33 through the ultraviolet objective lens 40, half mirror 64 and an imaging lens 65. Thus, the enlarged image of the semiconductor wafer is picked up by the ultraviolet light CCD camera 33. The image of the semiconductor wafer, picked up by the ultraviolet CCD camera 33 (will be referred to as "ultraviolet image" hereinafter) is sent to the image processing computer 30.

Figure 6:
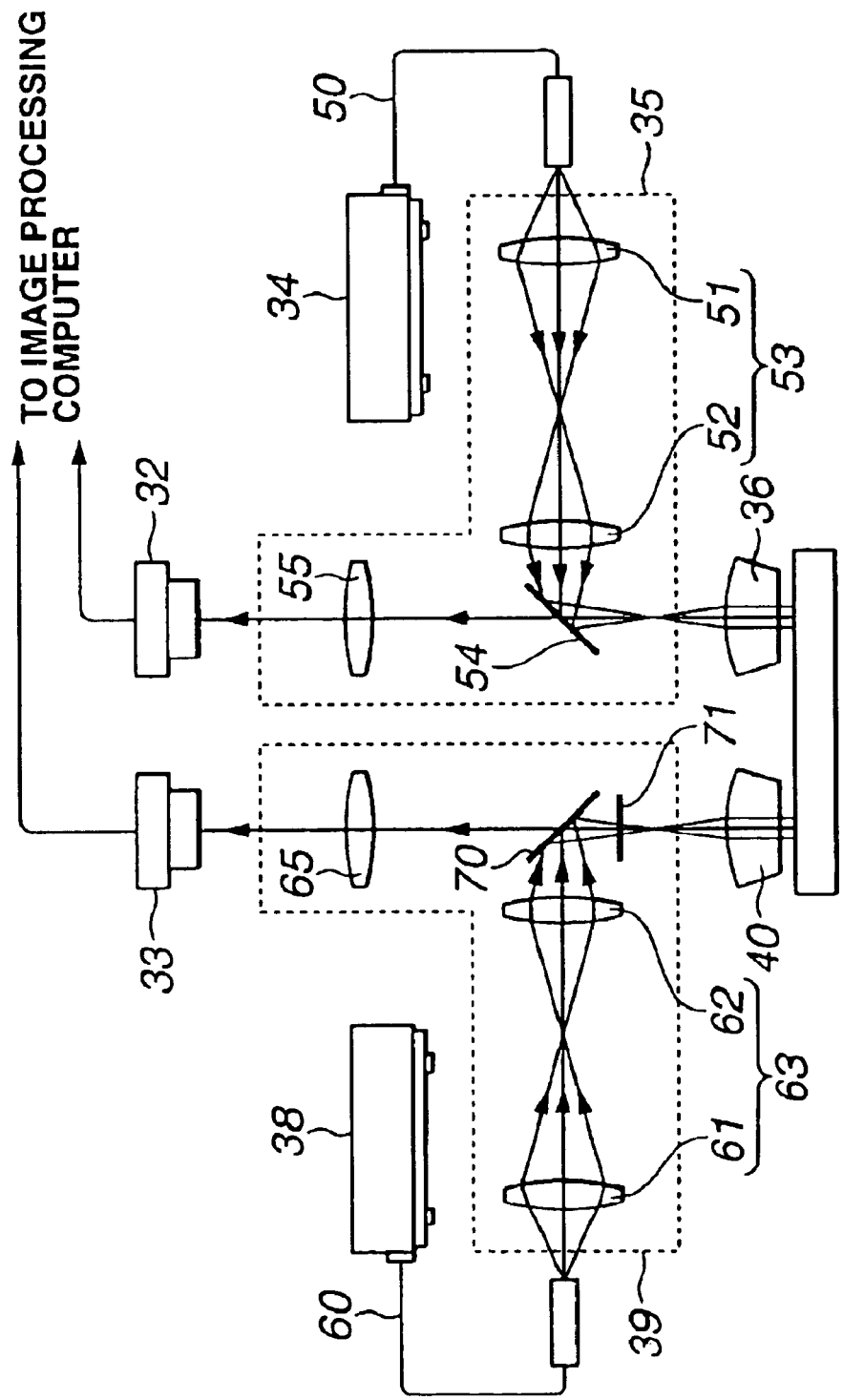
FIG. 6 shows another example of the construction of the optical system of the optical unit in the inspection equipment in FIG. 1.

As shown in FIG. 6, in the ultraviolet optical system 39, the half mirror 64 may be replaced with a polarizing beam splitter 70 and a quarter wave plate 71 may be disposed between the polarizing beam splitter 70 and ultraviolet objective lens 40. This construction of the ultraviolet optical system 39 will permit to use the ultraviolet laser with a higher efficiently.

With the inspection equipment 1 constructed as in the above, it is possible to inspect a semiconductor wafer by imaging it with an ultraviolet light having a shorter wavelength than a visible light and hence to detect and classify a finer defect than a defect which can be detected and classified with the visible light.

The above inspection equipment 1 includes bot the visible light optical system and ultraviolet optical system and thus permits both a low-resolution inspection of a semiconductor wafer with a visible light and a high-resolution inspection of the semiconductor with an ultraviolet light. Therefore, the inspection equipment 1 can also be used to detect and classify a large defect by the low-resolution inspection with a visible light while detecting and classifying a fine defect by the high-resolution inspection with an ultraviolet light.

In the above inspection equipment 1, the ultraviolet objective lens 40 should preferably have a large numerical aperture NA, for example, of more than 0.9. The ultraviolet objective lens 40 having a larger numerical aperture NA will permit to defect a finer defect.

If the defect of a semiconductor wafer is just a concavity or convexity with no color information such as a scratch, it can hardly be viewed with a non-coherent light. However, using a highly coherent light such as a laser light makes it possible to clearly view any defect being just a concavity or convexity having no color information such as a scratch since a coherence of light will take place near a step of the concavity or concavity. Since the inspection equipment 1 uses the ultraviolet laser source 38 which emits an ultraviolet laser light, it can definitely detect even a defect which is just a concavity or convexity with no color information such as a scratch. More specifically, using the ultraviolet laser (coherent light) emitted from the ultraviolet laser source 38, the inspection equipment 1 can easily detect a phase information different to detect with the visible light (incoherent light) from the halogen lamp 34.

Figure 7:
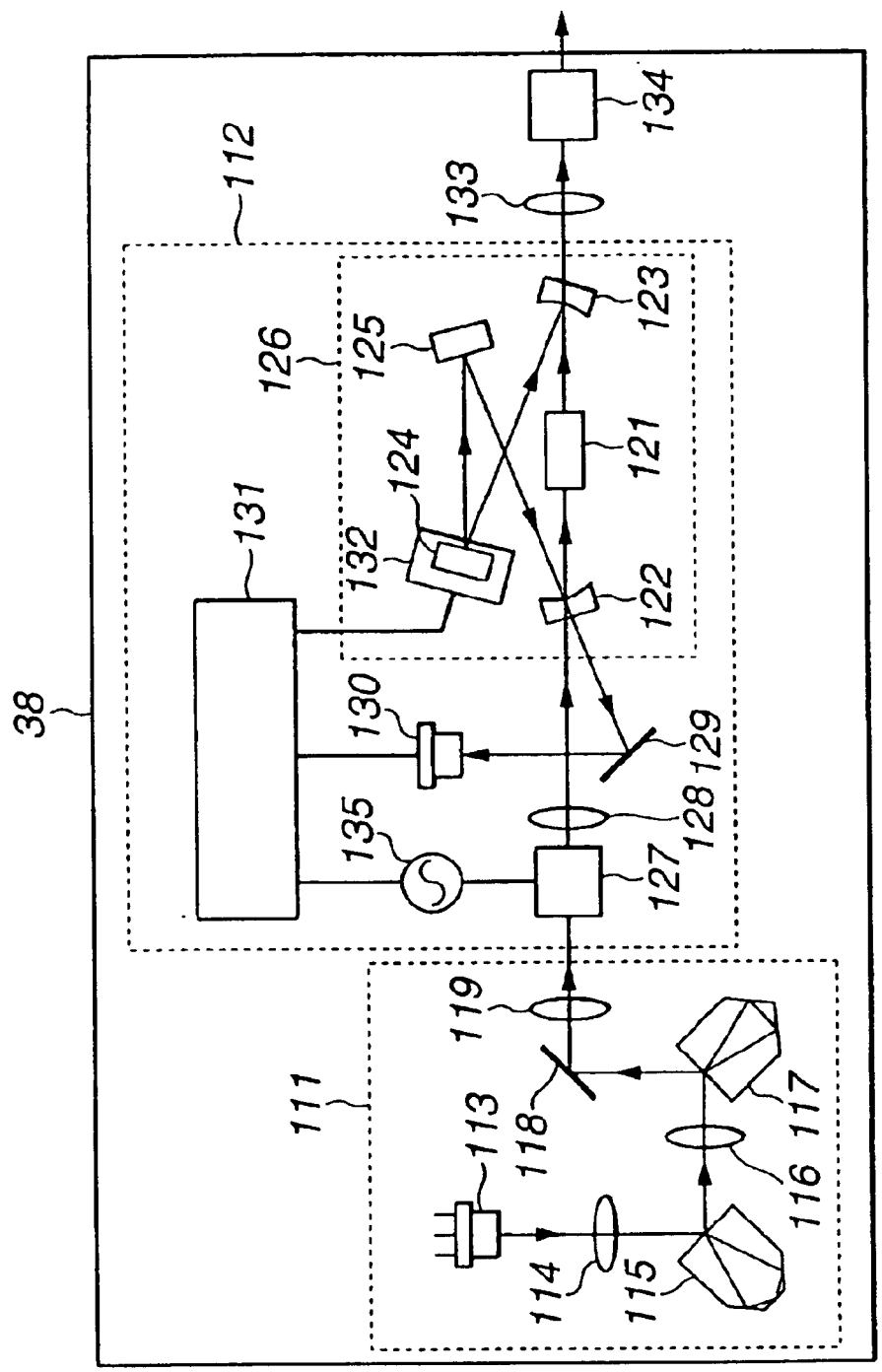
FIG. 7 shows an example of the construction of an Ultraviolet laser source used in the inspection equipment in FIG. 1.

Referring now to FIG. 7, there is illustrated an example of the construction of the ultraviolet laser source 38 used in the inspection equipment 1 in FIG. 1. The ultraviolet laser source 38 will be described in further detail below with reference to FIG. 7.

The ultraviolet laser source 38 shown in FIG. 7 generates an ultraviolet laser light by changing the wavelength of a laser light from a solid laser source. The ultraviolet laser source 38 includes a green laser light generator 111, and an ultraviolet laser light generator 112 to generate an ultraviolet laser light by changing the wavelength of a green laser light from the green laser generator 111.

The green laser light generator 111 emits a high power laser light having a wavelength $\lambda$ of 808 nm from a semiconductor laser 113. The high power laser light is condensed by a condenser lens 114 and incident upon a non-planer monolithic ring type Nd:YAG laser 115 which will thus be excited by the laser light as an excitation light to generate an infrared laser light having a wavelength $\lambda$ of 1064 nm. The Nd: YAG laser 115 is applied with an external magnetic field. Thus the Nd:YAG laser 115 oscillates only in one direction in a single longitudinal mode. This principle of laser generation is disclosed in the U.S. Pat. No. 4,749,842 for example.

According to the present invention, the Nd:YAG laser 115 is a monolithic ring type one. An optical resonator of the monolithic ring type shows a high stability of oscillation and an excellent temporal coherence as described in t. Kane et al Opt Lett Vol. 10 (1985), p65. In this Nd:YAG laser 115, the optical path in the resonator should preferably be non-planer. Owing to the non-planer optical path in the resonator, infrared laser light can be generated more stability.

The infrared laser light emitted from the Nd:YAG laser 115 is incident upon a monolithic ring type MgO:LN crystal 117 through a mode matching lens 116. When irradiated with the infrared laser light having the wavelength $\lambda$ of 1064 nm, the MgO:LN crystal 117 generates a second harmonic whose wavelength $\lambda$ is 532 nm. The MgO:LN crystal 117 forms an optical resonator adapted for the infrared laser light having the wavelength $\lambda$ of 1064 nm. Using the high power density inside the optical resonator, a highly efficient wavelength can be changed of a continuous wave. More particularly, by constructing the optical resonator with the wavelength of the infrared laser light made to coincide with a resonant wavelength inside the MgO:LN crystal 117, the second harmonic can be generated at an efficiency as high as 65%.

Since the second harmonic is generated by the MgO:LN crystal 117, the green laser light having the wavelength $\lambda$ of 532 mm acquired by changing the wavelength of the infrared laser light having the wavelength $\lambda$ of 1064 nm, is reflected by a light reflecting mirror 118 and shaped by a lens 119 to have a predetermined beam diameter, and then emitted from the green laser light generator 111.

The green laser light generator 111 constructed as in the above can generate a green laser light having an excellent temporal coherence with an extremely high efficiency. In the green laser light generator 111, when a laser light having a power of 1W is emitted from the semiconductor laser 113, the Nd:YAG laser 115 will generate an infrared laser light of about 500 mW while the MGO:LN crystal 117 will generate a green laser light of around 200 mW. As mentioned above, the green laser light generator 111 assures a very high efficiency of laser generation. Further, the electric efficiency of the semiconductor laser 113 is much higher than that of the gas laser, etc. It is on the order of 30%. Therefore, the green laser light generator 111 consumes only a small power even including the power consumption by the controller circuit, etc.

The green laser light thus generated by the green laser light generator 111 is incident upon the ultraviolet laser light generator 112. Using a $\beta$-$BaB_2O_4$ (will be referred to as "BBO" hereinafter) 121 being a nonlinear optical element, the ultraviolet laser light generator 112 generates a second harmonic of the green laser light, to thereby generate an ultraviolet laser light having a wavelength $\lambda$ of 266 nm. That is, taking the green laser light as a basic wave, the BBO 121 generates an ultraviolet laser light as a second harmonic of the green laser light.

The BBO 121 is transparent to a light having a wavelength $\lambda$ up to a far ultraviolet of 190 nm in wavelength $\lambda$, is strong against a laser damage and has a large birefringence. Therefore, it can generate a second harmonic in a wide range, and thus it is very suitable for use as a second harmonic generating element for the ultraviolet zone. However, for generation of a second harmonic having the wavelength $\lambda$ of 266 nin by the BBO 121, a rotational phase matching is required. Since a temperature phase matching as in the MgO:LN crystal 117 is impossible, it is difficult to generate the second harmonic using a monolithic ring type crystal as in the green laser light generator 111. In this situation, the ultraviolet laser light generator 112 generates the second harmonic by an external resonance using a ring type optical resonator 126 consisting of four independent mirrors 122, 123, 124 and 125.

The basic wave (green laser light) incident upon the ultraviolet laser light generator 112 is further incident upon the optical resonator 126 through a phase modulator 127 and mode matching lens 128. As mentioned above, the optical resonator 126 consists of the first to fourth mirrors 122 to 125, and the BBO 121 is disposed between the first and second mirrors 122 and 123.

Then, the basic wave is introduced into the optical resonator 126 through the first mirror 122. At this time, a part of the basic wave is reflected by the first mirror 122, and further reflected by a mirror 129 towards a photodetector 130 which will thus detect the basic wave. On the other band, the basic wave introduced into the optical resonator 126 through the first mirror 122 goes first towards the second mirror 123 through the BBO 121, next reflected by the second mirror 123 towards the third mirror 124, then reflected by the third mirror 124 towards the fourth mirror 125, further reflected by the fourth mirror 125 towards the first mirror 122, and thereafter reflected by the first mirror 122 towards the second mirror 123 again through the BBO 121.

The basic wave reflected by the first mirror 122 of the optical resonator 126 is detected by the photodetector 130 as having previously been described. A detection signal from the photodetector 130 is sent to a control circuit 131. In the ultraviolet laser light generator 112, the phase modulator 127 modulates the phase of the basic wave incident upon the optical resonator 126 by a modulation signal from a phase modulator drive circuit 135. Making a synchronous detection of the detection signal with the modulation signal, the control circuit 131 detects an error signal indicative of an optical path phase difference of the optical resonator 126, and drives, based on the error signal, an electromagnetic actuator 132 to control the position of the third mirror 124 continuously with so a high accuracy that the resonator length of the optical resonator 126 always meets the resonance conditions.

With the position of the third mirror 124 controlled continuously with a high accuracy as in the above, the resonator length of the optical resonator 126 can be controlled with an accuracy as high as one several hundredths of the light wavelength even if the optical resonator 126 consists of the plurality of independent mirrors 122 to 125. With the resonator length of the optical resonator 126 thus controlled with the high accuracy to meet the resonance conditions, the BBO 121 can generate the second harmonic very efficiently.

In the optical resonator 126, the BBO 121 is provided thereon with a reflection preventive layer to reduce the resonator loss. Also, to reduce the resonator loss, each of the second to fourth mirrors 123 to 125 forming together the optical resonator 126 is a mirror having a reflectance as high as 99.9%. Owing to the reflection preventive layer of the BBO 121 and the high reflectance of 99.9% of the second to fourth mirrors 123 to 125, the resonator loss of the optical resonator 126 can be limited to less than about 0.5%.

The ultraviolet laser light generator 112 constructed as in the above can generate an ultraviolet laser light excellent in temporal coherence with an extremely high efficiency. Actually, with the green laser light from the green laser light generator 111, incident upon the ultraviolet laser light generator 112, set to have a power of 200 mW, an ultraviolet laser light was generated by the ultraviolet laser light generator 112. An ultraviolet laser light having a power of about 50 mW could be provided in this case.

Since the ultraviolet light has a high photon energy, the mirrors and BBO forming together the optical resonator will possibly be deteriorated if it is tried to generate an ultraviolet laser light based on a second harmonic generated by the BBO provided in the optical resonator. Therefore, the conventional laser source adapted to generate an ultraviolet laser light based on a second harmonic generated by the BBO provided in the optical resonator has a short service life and is not so highly reliable. It is difficult to use the laser source in measuring instruments.

However, the Applicant of the present invention ascertained that by improving the growth of the BBO crystal, improving the reflection preventive laser applied to the BBO, optimizing the light spot size incident upon the BBO, cleaning the inside of the optical resonator and optimizing the atmosphere inside the optical resonator, a sufficient reliability and service life of the laser source could be attained even a second harmonic was generated by the BBO 121 provided in the optical resonator 126 as shown in FIG. 7. More specifically, it was provided that the above improvements and optimizations contributed to the fact that the laser source using the BBO 121 could stably generate an ultraviolet having a power of 100 mW for more than 1,000 hours and an ultraviolet laser light having a power of 30 mW for more than 5,000 hours. Based on these results, it can be estimated that the laser source using the BBO 121 will be able to stably generate an ultraviolet laser light having a power of 20 mW for about 10,000 hours. This service life will assure that the laser source can be a substantially maintenance-free one which can be used as a light source in an inspection equipment in practice.

The ultraviolet laser light generated by the ultraviolet laser light generator 112 as in the above is passed through a collimator lens 133 which will shape the laser light into a parallel light. The parallel light is shaped into a beam shaping by an anamorphic prism pair 134 and then emitted from an ultraviolet laser light source 38. Note that the anamorphic prism pair 134 shapes the ultraviolet laser light emitted from the ultraviolet laser source 38 into a beam whose spot has a nearly circular section. On the other hand, the ultraviolet laser light emitted from the optical resonator 126 is a beam whose section is made elliptic under the walk-off effect of the birefringence by the BBO 121. Therefore, before being emitted from the ultraviolet laser source 38, the ultraviolet laser light is shaped by the anamorphic prism pair 134 into a beam whose spot has a nearly circular section.

The ultraviolet laser source 38 constructed as in the above generates an ultraviolet laser light by the two-step changing of the laser light from the solid laser source (Nd:YAG laser 115) based on the second harmonic by the nonlinear optical elements (MgO:LN crystal 117 and BBO 121). Namely, the ultraviolet laser source 38 is a all solid ultraviolet laser source which generates an ultraviolet laser light by the solid optical elements only.

The ultraviolet laser source 38 formed from only the solid optical elements is a compact, highly efficient, low power consumption, highly stable and high beam quality one. Further, the ultraviolet laser source 38 can provide an ultraviolet laser light excellent in temporal coherence.

Note that for a laser source for generation of an ultraviolet laser light, there is available a gas laser such as excimer laser, argon laser or the like. However, the gas laser is not advantageous in its large volume, low efficiency and high power consumption. An argon laser for a laser light having a wavelength of 351 nm for example generates the laser light with an efficiency of less than 0.001%. The above-mentioned ultraviolet laser source 38 can generate an ultraviolet laser light with a high efficiency and can be designed rather compact in comparison with the argon laser.

Further to the above, the argon laser is disadvantageous in that a large amount of cooling water is required. When the cooling water is circulated, a vibration will take place. Thus, the argon laser requiring the large amount of cooling water is not suitable for use in any inspection equipment to inspect a fine structure. Moreover, the argon laser cannot generate a laser light having a stable wavelength. The excimer laser needs a fluoride gas which is dangerous. Further, since the excimer laser generates a pulsed laser light having a high-peak power, it is not suitable for use as a laser source in the inspection equipment 1 adapted to image a semiconductor wafer for inspection.

The ultraviolet laser source 38 solves the above-mentioned problems which would be raised when the excimer laser and argon laser are used, by changing the wavelength of a laser light from the solid laser source to provide an ultraviolet laser light.

Next, the procedure for inspecting a semiconductor wafer by the inspection equipment 1 according to the present invention will be described herebelow with reference to the flow charts shown in FIGS. 8 through 11. The flow charts in FIGS. 8 to 11 show operations effected after a semiconductor wafer as a specimen is placed on the inspection stage 11. It is assumed herein that the semiconductor wafer has many similar device patterns formed therein and an image of an area of the semiconductor wafer where there is a defect (defect image) and an image of other area (reference image) are picked up and compared between them for detection ad classification of the defect.

Figure 8:
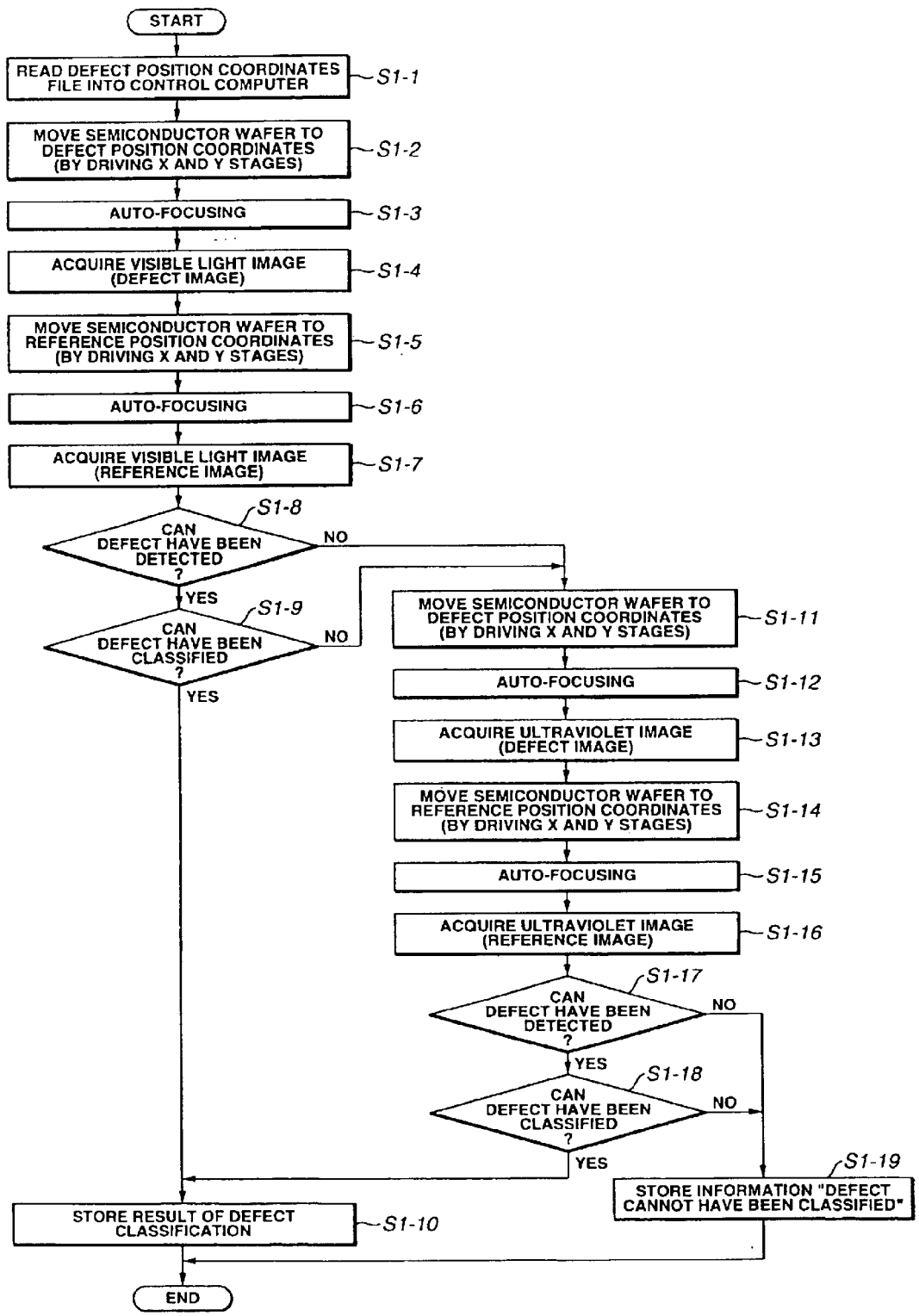
FIG. 8 is a flow chart of operations effected in an example of the procedure for inspecting a semiconductor wafer by the inspection equipment according to the present invention.

Referring now to FIG. 8, there is given a flow chart of operations effected in the procedure for inspecting a semiconductor wafer by the inspection equipment 1 according to the present invention. This flow chart shows an example of the inspecting procedure in which when the position of a defect on the semiconductor wafer is already known, the detect is detected and classified by the inspection equipment 1.

In this example, a defect position coordinates file is first read into the control computer 31 at step S1-1. The defect position coordinates file has described therein information on the position of a defect on the semiconductor wafer. It is a file having been prepared by preliminarily measuring the position of a defect on the semiconductor wafer by means of a defect detector or the like. The defect position coordinates file thus prepared is read into the control computer 31.

Next, at step S1-2, the X and Y stages 14 and 15 are driven by the control computer 31 to move the semiconductor wafer to the defect position coordinates indicated in the defect position coordinates file so that a to-be-inspected area of the semiconductor wafer comes into the field of view of the visible light objective lens 36.

Next, at step S1-3, the control computer 31 drives the visible light auto-focus controller 37 to automatically focus the visible light objective lens 36.

Next, at step S1-4, an image of the semiconductor wafer is picked up by the visible light CCD camera 32 and the visible image thus picked up is sent to the image processing computer 30. Note that the picked-up visible image is an image at defect position coordinates indicated in the defect position coordinates file, namely, an image of an area where a defect exists (will be referred to as "defect image" hereinafter).

Next, at step S1-5, the control computer 31 drives the X and Y stages 14 and 15 to move the semiconductor wafer to reference position coordinates for the reference area of the semiconductor wafer to enter into the field of view of the visible light objective lens 36. The reference area is an area of the semiconductor wafer other than the to-be-inspected area and has formed therein a device pattern similar to the device pattern formed in the to-be-inspected area of the semiconductor wafer.

Next, at step S1-6, the control computer 31 drives the visible light auto-focus controller 37 to automatically focus the visible light objective lens 36.

Next, at step S1-7, an image of the semiconductor wafer is picked up by the visible light CCD camera 32 and the visible image thus picked up is sent to the image processing computer 30. Note that the picked-up visible image is an image of an area having formed therein a device pattern similar to the device pattern formed in the to-be-inspected area of the semiconductor wafer (will be referred to as "reference image" hereinafter).

Next, at step S1-8, the image processing computer 30 makes a comparison between the defect image acquired at step S1-4 and the reference image acquired at step S1-7 to detect a defect from the defect image. When a defect can have been detected, the operation proceeds to step S1-9. When no defect can have been detected, the operation goes to step S1-1.

At step S1-9, the image processing computer 30 examines what the detected defect is to classify the defect. When the defect can have been classified, the operation goes to step S1-10. When the defect cannot have been classified, the operation goes to step S1-11.

At step S1-10, the result of the defect classification is stored. It is stored in a storage device, for example, connected to the image processing computer 30 and control computer 31. The result of the defect classification may be transferred to and stored into any other computer connected to the image processing computer 30 and control computer 31 via a network.

Upon completion of the operation at step S1-10, the classification of the defect in the semiconductor wafer will be complete. Thus, the inspecting procedure is ended. However, if a plurality of defects exists on the semiconductor wafer, the operation may be returned to step S1-2 where other defects are to be detected and classified.

On the other hand, if no defect can have been detected at step S1-8 or if no defect classification can have been made at step S1-9, the operation proceeds to step S1-11 where the ultraviolet light is used to pick up an image of the semiconductor wafer for defect detection and classification.

In this case, at step S1-11, the control computer 31 drives the X and Y stages 14 and 15 to move the semiconductor wafer to the defect position coordinates indicated in the defect position coordinates file for the to-be-inspected area of the semiconductor wafer to enter into the field of view of the ultraviolet objective lens 40.

Next, at step S1-12, the control computer 31 drives the ultraviolet auto-focus controller 41 to automatically focus the ultraviolet objective lens 40.

Next, at step S1-13, an image of the semiconductor wafer is picked up by the ultraviolet CCD camera 33 and the ultraviolet image thus picked up is sent to the image processing computer 30. Note that the picked-up ultraviolet image is an image at defect position coordinates indicated in the defect position coordinates file, namely, a defect image. Also, the defect image is picked up using an ultraviolet light having a shorter wavelength that the visible light and with a higher resolution than that with the visible light.

Next, at step S1-14, the control computer 31 drives the X and Y stages 14 and 15 to move the semiconductor wafer to the reference position coordinates for the reference area of the semiconductor wafer to enter into the field of view of the ultraviolet objective lens 40. The reference area is an area of the semiconductor wafer other than the to-be-inspected area and has formed therein a device pattern similar to the device pattern formed in the to-be-inspected area of the semiconductor wafer. Next, at step S1-15, the control computer 31 drives the ultraviolet auto-focus controller 41 to automatically focus the ultraviolet objective lens 40. Next, at step S1-16, an image of the semiconductor wafer is picked up by the ultraviolet CCD camera 33 and the ultraviolet image thus picked up is sent to the image processing computer 30. Note that the picked-up ultraviolet image is an image of an area in which a device pattern similar to that formed in the to-be-inspection area of the semiconductor wafer is formed, namely, a reference area. Also, the reference image is picked up using an ultraviolet light having a shorter wavelength that the visible light and with a higher resolution than that with the visible light.

Next, at step S1-17, the image processing computer 30 makes a comparison between the defect image acquired at step S1-13 and the reference image acquired at step S1-16 to detect a defect from the defect image. When a defect can be detected, the operation proceeds to step S1-18. When no defect can be detected, the operation goes to step S1-19.

At step S1-18, the image processing computer 30 examines what the detected defect is to classify the defect. When the defect can have been classified, the operation goes to step S1-10 where the result of the defect classification is to be stored as mentioned above. When the defect cannot have been classified, the operation goes to step S-19.

At step S-19, information that the defect cannot have been classified is stored. The information is stored in the storage device, for example, connected to the image processing computer 30 and control computer 31. The information may be transferred to and stored into any other computer connected to the image processing computer 30 and control computer 31 via a network.

Following the above procedure, first the image picked up by the visible light CCD camera 32 is processed and analyzed to inspect the semiconductor wafer with a low resolution. When no defect can have been detected and classified using the visible light, the image picked up by the ultraviolet CCD camera 33 is processed and analyzed to inspect the semiconductor wafer with a high resolution. Thus, a finer defect can be detected and classified than in the defect detection and classification using only the visible light.

In the low resolution inspection using the visible light, a wider area can be imaged at a time. So, when the defect is sufficiently large, the low resolution inspection of a semiconductor wafer using the visible light is more efficient. Therefore, the ultraviolet light is not initially used to detect and classify a defect but first the visible light is used to detect and classify a defect, whereby a semiconductor wafer can be inspected more efficiently.

Figure 9:
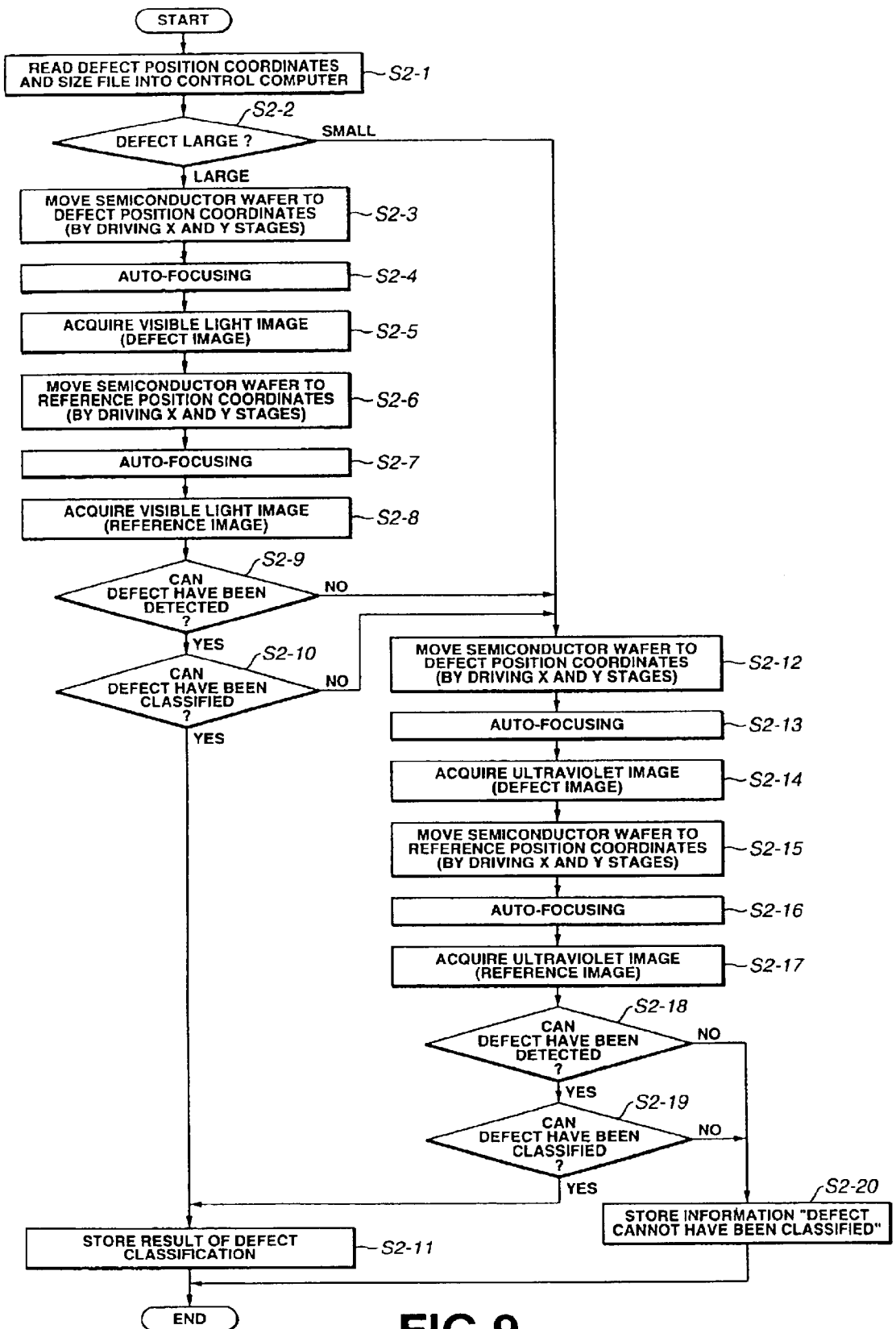
FIG. 9 is a flow chart of operations effected in another example of the procedure for inspecting a semiconductor wafer by the inspection equipment according to the present invention.

Referring now to FIG. 9, there is given a flow chart of operations effected in the procedure for inspecting a semiconductor wafer by the inspection equipment 1 according to the present invention. The flow chart in FIG. 9 shows another example of the inspecting procedure in which when the position and size of a defect on the semiconductor wafer are already known, the detect is detected and classified by the inspection equipment 1.

In this example, a defect position coordinates and defect size file is first read into the control computer 31 at step S2-1. The defect position coordinates and defect size file has described therein information on the position of a defect on the semiconductor wafer and size of the defect. It is a file having been prepared by preliminarily measuring the position and size of a defect on the semiconductor wafer by means of a defect detector or the like. The defect position coordinates and defect size file thus prepared is read into the control computer 31.

Next at step S2-2, the size of a defect on the semiconductor wafer is determined based on the file having been read at step S2-1. When the defect has a larger size than predetermined, the operation proceeds to step S2-3. When the defect has a smaller size then predetermined, the operation goes to step S2-12.

The defect size judgment is effected based on a resolution which can be attained when the ultraviolet light is used to image the semiconductor wafer. More specifically, assuming that a defect in the semiconductor wafer has a diameter A, the wavelength of the ultraviolet light emitted from the ultraviolet laser source 38 is $\lambda$ and the numerical aperture NA of the ultraviolet objective lens 40 is NA, when $A \geq 2 \times \lambda/NA$, the operation goes to step S2-3. If $A < 2 \times \lambda/NA$, the operation goes to step S2-12.

When $\lambda=0.266$ $\mu$m and NA=0.9, A=0.6 $\mu$m. This defect size equals to the size of visible light spot. Therefore, it is also a minimum defect size which can be detected using the visible light. In other words, the percent of detection of smaller defects will be considerably lower. On the other hand, defects of such small size can satisfactorily be detected using the ultraviolet light. Therefore, it is very preferable to take the above defect size or diameter A ($=2\times\lambda/NA$) as a criterion with reference to which it should be judged whether the visible light or ultraviolet light is to be used for the defect inspection. This criterion was found through many experiments effected by the Inventors of the present invention. Based on the criterion, the defect detection with the visible light and/or that with the ultraviolet light can effectively be selected to detect almost all defects ranging from large to small with a high efficiency.

At step S2-3, the control computer 31 drives the X and Y stages 14 and 15 to move the semiconductor wafer to the defect position coordinates indicated in the defect position coordinates file for the to-be-inspected area of the semiconductor wafer to enter into the field of view of the visible light objective lens 36.

Next, at step S2-4, the control computer 31 drives the visible light auto-focus controller 37 to automatically focus the visible light objective lens 36.

Next, at step S2-5, an image of the semiconductor wafer is picked up by the visible light CCD camera 32 and the visible image thus picked up is sent to the image processing computer 30. Note that the picked-up visible image is an image at defect position coordinates indicated in the defect position coordinates file, namely, a defect image.

Next, at step S2-6, the control computer 31 drives the X and Y stages 14 and 15 to move the semiconductor wafer to reference position coordinates for the reference area of the semiconductor wafer to enter into the field of view of the visible light objective lens 36. The reference area is an area of the semiconductor wafer other than the to-be-inspected area and has formed therein a device pattern similar to the device pattern formed in the to-be-inspected area of the semiconductor wafer.

Next, at step S2-7, the control computer 31 drives the visible light auto-focus controller 37 to automatically focus the visible light objective lens 36.

Next, at step S2-8, an image of the semiconductor wafer is picked up by the visible light CCD camera 32 and the visible image thus picked up is sent to the image processing computer 30. Note that the picked-up visible image is an image of an area having formed therein a device pattern similar to the device pattern formed in the to-be-inspected area of the semiconductor wafer, that is a reference image.

Next, at step S2-9, the image processing computer 30 makes a comparison between the defect image acquired at step S2-5 and the reference image acquired at step S2-8 to detect a defect from the defect image. When a defect can be detected, 4 the operation proceeds to step S2-10. When no defect can be detected, the operation goes to step S2-12.

At step S2-10, the image processing computer 30 examines what the detected defect is to classify the defect. When the defect can have been classified, the operation goes to step S2-11. When the defect cannot have been classified, the operation goes to step S2-12.

At step S2-11, the result of the defect classification is stored. It is stored in a storage device, for example, connected to the image processing computer 30 and control computer 31. The result of the defect classification may be transferred to and stored into any other computer connected to the image processing computer 30 and control computer 31 via a network.

Upon completion of the operation at step S2-11, the classification of the defect in the semiconductor wafer will be complete. Thus, the inspecting procedure is ended. However, if a plurality of defects exists on the semiconductor wafer, the operation may be returned to step S2-2 where other defects are to be detected and classified.

On the other hand, if the detected defect is judged at step S2-2 to have a size smaller than predetermined, if no defect cannot be detected at step S2-9 or if the defect cannot have been classified at step S2-10, the operation proceeds to step 2-12 and subsequent steps, where the ultraviolet light is used to pick up an image of the semiconductor wafer with a higher resolution for defect detection and classification.

In this case, first at step S2-12, the control computer 31 drives the X and Y stages 14 and 15 to move the semiconductor wafer to the defect position coordinates indicated in the defect position coordinates file for the to-be-inspected area of the semiconductor wafer to enter into the field of view of the ultraviolet objective lens 40.

Next, at step S2-13, the control computer 31 drives the ultraviolet auto-focus controller 41 to automatically focus the ultraviolet objective lens 40.

Next, at step S2-14, an image of the semiconductor wafer is picked up by the ultraviolet CCD camera 33 and the ultraviolet image thus picked up is sent to the image processing computer 30. Note that the picked-up ultraviolet image is an image at defect position coordinates indicated in the defect position coordinates file, namely, a defect image. Also, the defect image is picked up using an ultraviolet light having a shorter wavelength that the visible light and with a higher resolution than that with the visible light.

Next, at step S2-15, the control computer 31 drives the X and Y stages 14 and 15 to move the semiconductor wafer to the reference position coordinates for the reference area of the semiconductor wafer to enter into the field of view of the ultraviolet objective lens 40. The reference area is an area of the semiconductor wafer other than the to-be-inspected area and has formed therein a device pattern similar to the device pattern formed in the to-be-inspected area of the semiconductor wafer.

Next, at step S2-16, the control computer 31 drives the ultraviolet auto-focus controller 41 to automatically focus the ultraviolet objective lens 40.

Next, at step S2-17, an image of the semiconductor wafer is picked up by the ultraviolet CCD camera 33 and the ultraviolet image thus picked up is sent to the image processing computer 30. Note that the picked-up visible light image is an image of an area in which a device pattern similar to that formed in the to-be-inspection area of the semiconductor wafer is formed, namely, a reference area. Also, the reference image is picked up using the ultraviolet light having a shorter wavelength that the visible light and with a lower resolution than that with the visible light.

Next, at step S2-18, the image processing computer 30 makes a comparison between the defect image acquired at step S2-14 and the reference image acquired at step S2-17 to detect a defect from the defect image. When a defect can be detected, the operation proceeds to step S2-19. When no defect can be detected, the operation goes to step S2-20.

At step S1-19, the image processing computer 30 examines what the detected defect is to classify the defect. When the defect can have been classified, the operation goes to step S2-11 where the result of the defect classification is to be stored as mentioned above. When the defect cannot have been classified, the operation goes to step S2-20.

At step S2-20, information that the defect cannot have been classified is stored. The information is stored in the storage device, for example, connected to the image processing computer 30 and control computer 31. The information may be transferred to and stored into any other computer connected to the image processing computer 30 and control computer 31 via a network.

When the defect size is known, the inspection with a low resolution using the visible light is not effected for small defects but the inspection with a high resolution using the ultraviolet light is initially effected for the small defects. Thus the defect inspection can efficiently be done.

Figure 10:
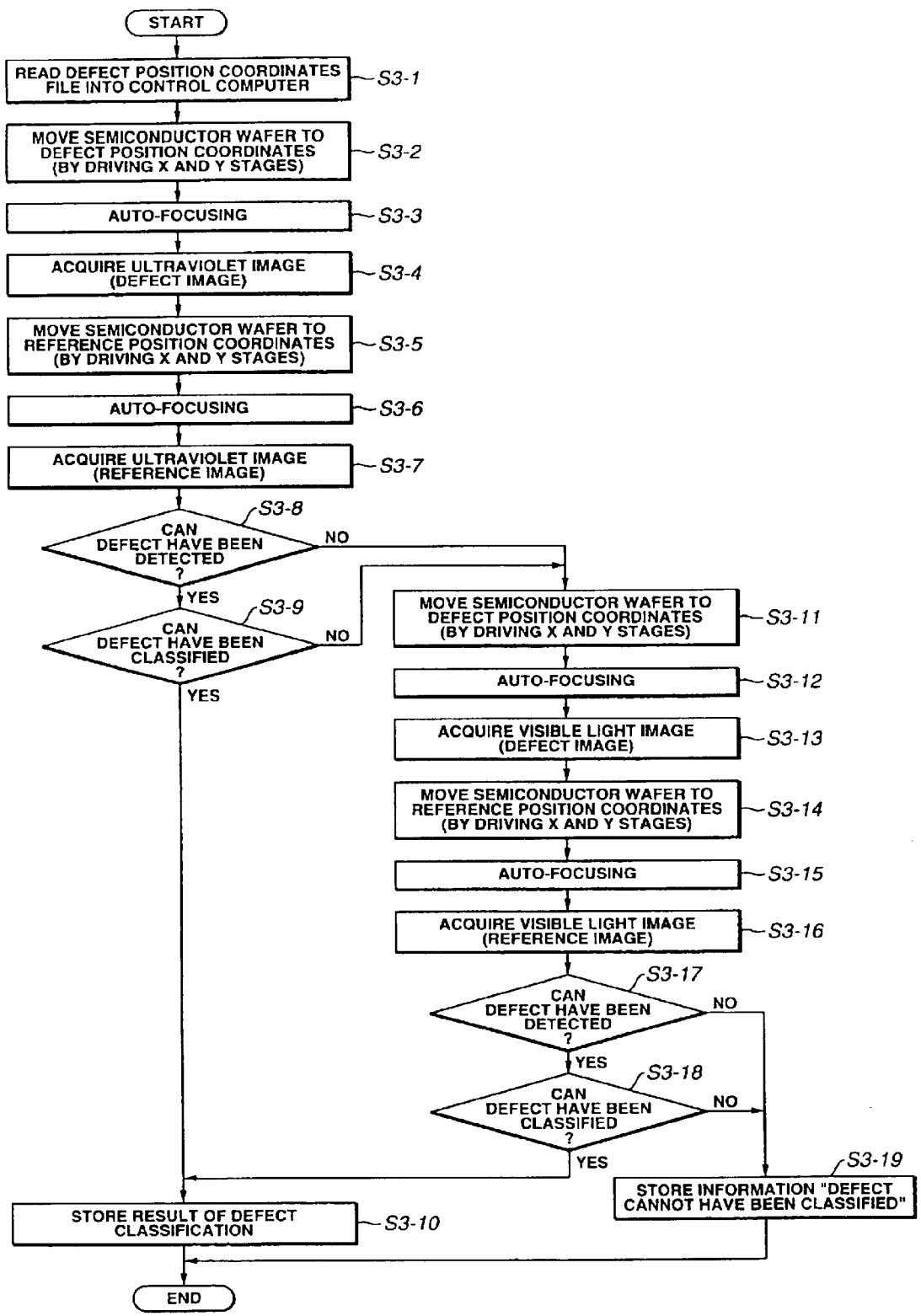
FIG. 10 is a flow chart of operations effected in a still another example of the procedure for inspecting a semiconductor wafer by the inspection equipment according to the present invention.

Referring now to FIG. 10, there is also given a flow chart of operations effected in the procedure for inspecting a semiconductor wafer by the inspection equipment 1 according to the present invention. This flow chart shows a yet another example of the inspecting procedure in which when the position of a defect on the semiconductor wafer is already known, the detect is detected and classified by the inspection equipment 1.

In this example, a defect position coordinates file is first read into the control computer 31 at step S3-1. The defect position coordinates file has described therein information on the position of a defect on the semiconductor wafer. It is a file having been prepared by preliminarily measuring the position of a defect on the semiconductor wafer by means of a defect detector or the like. The defect position coordinates file thus prepared is read into the control computer 31.

Next, at step S3-2, the X and Y stages 14 and 15 are driven by the control computer 31 to move the semiconductor wafer to the defect position coordinates indicated in the defect position coordinates file so that a to-be-inspected area of the semiconductor wafer comes into the field of view of the ultraviolet objective lens 40.

Next, at step S3-3, the control computer 31 drives the ultraviolet auto-focus controller 41 to automatically focus the ultraviolet objective lens 40.

Next, at step S3-4, an image of the semiconductor wafer is picked up by the ultraviolet CCD camera 33 and the ultraviolet image thus picked up is sent to the image processing computer 30. Note that the picked-up ultraviolet image is an image at defect position coordinates indicated in the defect position coordinates file, namely, a defect image.

Next, at step S3-5, the control computer 31 drives the X and Y stages 14 and 15 to move the semiconductor wafer to the reference position coordinates for the reference area of the semiconductor wafer to enter into the field of view of the ultraviolet objective lens 40. The reference area is an area of the semiconductor wafer other than the to-be-inspected area and has formed therein a device pattern similar to the device pattern formed in the to-be-inspected area of the semiconductor wafer.

Next, at step S3-6, the control computer 31 drives the ultraviolet auto-focus controller 41 to automatically focus the ultraviolet objective lens 40.

Next, at step S3-7, an image of the semiconductor wafer is picked up by the ultraviolet CCD camera 33 and the ultraviolet image thus picked up is sent to the image processing computer 30. Note that the picked-up ultraviolet image is an image of an area in which a device pattern similar to that formed in the to-be-inspection area of the semiconductor wafer is formed, namely, a reference area.

Next, at step S3-8, the image processing computer 30 makes a comparison between the defect image acquired at step S3-4 and the reference image acquired at step S3-7 to detect a defect from the defect image. When a defect can be detected, the operation proceeds to step S3-9. When no defect can be detected, the operation goes to step S3-11.

At step S3-9, the image processing computer 30 examines what the detected defect is to classify the defect. When the defect can have been classified, the operation goes to step S3-10. When the defect cannot have been classified, the operation goes to step S3-11.

At step S3-10, the result of the defect classification is stored. It is stored in a storage device, for example, connected to the image processing computer 30 and control computer 31. The result of the defect classification may be transferred to and stored into any other computer connected to the image processing computer 30 and control computer 31 via a network.

Upon completion of the operation at step S3-10, the classification of the defect in the semiconductor wafer will be complete. Thus, the inspecting procedure is ended. However, if a plurality of defects exists on the semiconductor wafer, the operation may be returned to step S3-2 where other defects are to be detected and classified.

On the other hand, if no defect can have been detected at step S3-8 or if no defect classification can have been done at step S3-9, the operation proceeds to step 3-11 and subsequent steps, where the ultraviolet light is used to pick up an image of the semiconductor wafer with a higher resolution for defect detection and classification.

In this case, first at step S3-11, the control computer 31 drives the X and Y stages 14 and 15 to move the semiconductor wafer to the defect position coordinates indicated in the defect position coordinates file for the to-be-inspected area of the semiconductor wafer to enter into the field of view of the visible light objective lens 36.

Next, at step S3-12, the control computer 31 drives the visible light auto-focus controller 37 to automatically focus the visible light objective lens 36.

Next, at step S3-13, an image of the semiconductor wafer is picked up by the visible light CCD camera 32 and the ultraviolet image thus picked up is sent to the image processing computer 30. Note that the picked-up visible light image is an image at defect position coordinates indicated in the defect position coordinates file, namely, a defect image. Also, the defect image is picked up using an visible light having a longer wavelength that the ultraviolet light and with a lower resolution than that with the ultraviolet light.

Next, at step S3-14, the control computer 31 drives the X and Y stages 14 and 15 to move the semiconductor wafer to reference position coordinates for the reference area of the semiconductor wafer to enter into the field of view of the visible light objective lens 36. The reference area is an area of the semiconductor wafer other than the to-be-inspected area and has formed therein a device pattern similar to the device pattern formed in the to-be-inspected area of the semiconductor wafer.

Next, at step S3-15, the control computer 31 drives the visible light auto-focus controller 37 to automatically focus the visible light objective lens 36.

Next, at step S3-16, an image of the semiconductor wafer is picked up by the visible light CCD camera 32 and the ultraviolet image thus picked up is sent to the image processing computer 30. Note that the picked-up visible light image is an image of an area in which a device pattern similar to that formed in the to-be-inspection area of the semiconductor wafer is formed, namely, a reference area. Also, the reference image is picked up using a visible light having a longer wavelength that the ultraviolet light and with a lower resolution than that with the ultraviolet light.

Next, at step S3-17, the image processing computer 30 makes a comparison between the defect image acquired at step S3-13 and the reference image acquired at step S3-16 to detect a defect from the defect image. When a defect can be detected, the operation proceeds to step S3-18. When no defect can be detected, the operation goes to step S3-19.

At step S3-18, the image processing computer 30 examines what the detected defect is to classify the defect. When the defect can have been classified, the operation goes to step S3-10 where the result of the defect classification is to be stored as mentioned above. When the defect cannot have been classified, the operation goes to step S3-19.

At step S3-19, information that the defect cannot have been classified is stored. The information is stored in the storage device, for example, connected to the image processing computer 30 and control computer 31. The information may be transferred to and stored into any other computer connected to the image processing computer 30 and control computer 31 via a network.

Following the above procedure, first the image picked up by the ultraviolet CCD camera 33 is processed and analyzed to inspect the semiconductor wafer with a high resolution. When no defect cannot be detected and classified using the ultraviolet light, the image picked up by the visible light CCD camera 32 is processed and analyzed to inspect the semiconductor wafer with a low resolution. Thus, a finer defect can be detected and classified than in the defect detection and classification using only the visible light.

Figure 11:
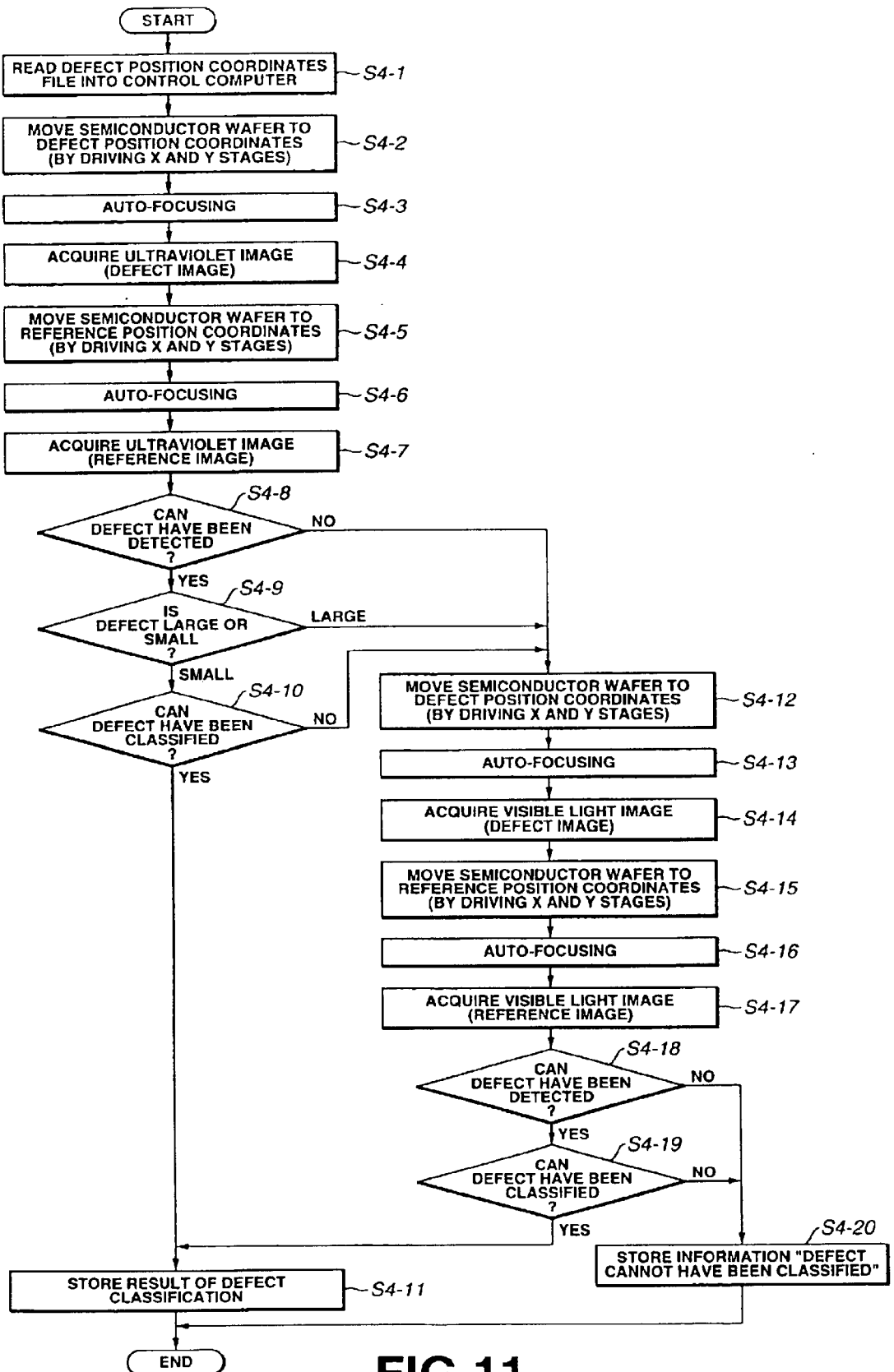
FIG. 11 is a flow chart of operations effected in a yet another example of the procedure for inspecting a semiconductor wafer by the inspection equipment according to the present invention.

Referring now to FIG. 11, there is also given a flow chart of operations effected in the procedure for inspecting a semiconductor wafer by the inspection equipment 1 according to the present invention. This flow chart shows a yet another example of the inspecting procedure in which when the position and size of a defect on the semiconductor wafer are already known, the detect is detected and classified by the inspection equipment 1.

In this example, a defect position coordinates file is first read into the control computer 31 at step S4-1. The defect position coordinates file has described therein information on the position of a defect on the semiconductor wafer. It is a file having been prepared by preliminarily measuring the position of a defect on the semiconductor wafer by means of a defect detector or the like. The defect position coordinates file thus prepared is read into the control computer 31.

Next, at step S4-2, the X and Y stages 14 and 15 are driven by the control computer 31 to move the semiconductor wafer to the defect position coordinates indicated in the defect position coordinates file so that a to-be-inspected area of the semiconductor wafer comes into the field of view of the ultraviolet objective lens 40.

Next, at step S4-3, the control computer 31 drives the ultraviolet auto-focus controller 41 to automatically focus the ultraviolet objective lens 40.

Next, at step S44, an image of the semiconductor wafer is picked up by the ultraviolet CCD camera 33 and the ultraviolet image thus picked up is sent to the image processing computer 30. Note that the picked-up ultraviolet image is an image at defect position coordinates indicated in the defect position coordinates file, namely, a defect image.

Next, at step S4-5, the control computer 31 drives the X and Y stages 14 and 15 to move the semiconductor wafer to the reference position coordinates for the reference area of the semiconductor wafer to enter into the field of view of the ultraviolet objective lens 40. The reference area is an area of the semiconductor wafer other than the to-be-inspected area and has formed therein a device pattern similar to the device pattern formed in the to-be-inspected area of the semiconductor wafer.

Next, at step S4-6, the control computer 31 drives the ultraviolet auto-focus controller 41 to automatically focus the ultraviolet objective lens 40.

Next, at step S4-7, an image of the semiconductor wafer is picked up by the ultraviolet CCD camera 33 and the ultraviolet image thus picked up is sent to the image processing computer 30. Note that the picked-up ultraviolet image is an image of an area in which a device pattern similar to that formed in the to-be-inspection area of the semiconductor wafer is formed, namely, a reference area.

Next, at step S4-8, the image processing computer 30 makes a comparison between the defect image acquired at step S4-4 and the reference image acquired at step S4-7 to detect a defect from the defect image. When a defect can be detected, the operation proceeds to step S4-9. When no defect can be detected, the operation goes to step S4-12.

Next at step S4-9, the size of a defect detected at step S4-8. When the defect has a larger size than predetermined, the operation proceeds to step S4-12. When the defect has a smaller size then predetermined, the operation goes to step S4-10.

The defect size judgment is effected based on a resolution which can be attained when the ultraviolet light is used to image the semiconductor wafer. More specifically, assuming that a defect in the semiconductor wafer has a diameter A, the wavelength of the ultraviolet light emitted from the ultraviolet laser source 38 is $\lambda$ and the numerical aperture NA of the ultraviolet objective lens 40 is NA, when $A \geq 2 \times \lambda/NA$, the operation goes to step S4-12. If $A<2\times\lambda/NA$, the operation goes to step S4-10.

When $\lambda=0.266$ $\mu$m and NA=0.9, A=0.6 $\mu$m. This defect size equals to the size of visible light spot. Therefore, it is also a minimum defect size which can be detected using the visible light. In other words, the percent of detection of smaller defects will be considerably lower. On the other hand, defects of such small size can satisfactorily be detected using the ultraviolet light. Therefore, it is very preferable to take the above defect size or diameter A (=2×λ/NA) as a criterion with reference to which it should be judged whether the visible light or ultraviolet light is to be used for the defect inspection. This criterion was found through many experiments effected by the Inventors of the present invention. Based on the criterion, the defect detection with the visible light and/or that with the ultraviolet light can effectively be selected to detect almost all defects ranging from large to small with a high efficiency.

At step S4-10, the image processing computer 30 examines what the detected defect is to classify the defect. When the defect can have been classified, the operation goes to step S4-11. When the defect cannot have been classified, the operation goes to step S4-12.

At step 4-11, the result of the defect classification is stored. It is stored in a storage device, for example, connected to the image processing computer 30 and control computer 31. The result of the defect classification may be transferred to and stored into any other computer connected to the image processing computer 30 and control computer 31 via a network.

Upon completion of the operation at step S4-11, the classification of the defect in the semiconductor wafer will be complete. Thus, the inspecting procedure is ended. However, if a plurality of defects exists on the semiconductor wafer, the operation may be returned to step S4-2 where other defects are to be detected and classified.

On the other hand, if no defect can have been detected at step S4-8, if the detected defect is judged at step S4-9 to have a size larger than predetermined, or if the defect cannot have been classified S4-10, the operation proceeds to step 4-12 and subsequent steps, where the visible light is used to pick up an image of the semiconductor wafer with a lower resolution for defect detection and classification.

In this case, first at step S4-12, the control computer 31 drives the X and Y stages 14 and 15 to move the semiconductor wafer to the defect position coordinates indicated in the defect position coordinates file for the to-be-inspected area of the semiconductor wafer to enter into the field of view of the visible light objective lens 36.

Next, at step S4-13, the control computer 31 drives the visible light auto-focus controller 37 to automatically focus the visible light objective lens 36.

Next, at step S4-14, an image of the semiconductor wafer is picked up by the visible light CCD camera 32 and the ultraviolet image thus picked up is sent to the image processing computer 30. Note that the picked-up visible light image is an image at defect position coordinates indicated in the defect position coordinates file, namely, a defect image. Also, the defect image is picked up using an visible light having a longer wavelength that the ultraviolet light and with a lower resolution than that with the ultraviolet light.

Next, at step S4-15, the control computer 31 drives the X and Y stages 14 and 15 to move the semiconductor wafer to reference position coordinates for the reference area of the semiconductor wafer to enter into the field of view of the visible light objective lens 36. The reference area is an area of the semiconductor wafer other than the to-be-inspected area and has formed therein a device pattern similar to the device pattern formed in the to-be-inspected area of the semiconductor wafer.

Next, at step S4-16, the control computer 31 drives the visible light auto-focus controller 37 to automatically focus the visible light objective lens 36.

Next, at step S4-17, an image of the semiconductor wafer is picked up by the visible light CCD camera 32 and the ultraviolet image thus picked up is sent to the image processing computer 30. Note that the picked-up visible image is an image of an area in which a device pattern similar to that formed in the to-be-inspection area of the semiconductor wafer is formed, namely, a reference area. Also, the reference image is picked up using a visible light having a longer wavelength that the ultraviolet light and with a lower resolution than that with the ultraviolet light.

Next, at step S4-18, the image processing computer 30 makes a comparison between the defect image acquired at step S4-14 and the reference image acquired at step S4-17 to detect a defect from the defect image. When a defect can be detected, the operation proceeds to step S4-19. When no defect can be detected, the operation goes to step S4-20.

At step S4-19, the image processing computer 30 examines what the detected defect is to classify the defect. When the defect can have been classified, the operation goes to step S4-11 where the result of the defect classification is to be stored as mentioned above. When the defect cannot have been classified, the operation goes to step S4-20.

At step S4-20, information that the defect cannot have been classified is stored. The information is stored in the storage device, for example, connected to the image processing computer 30 and control computer 31. The information may be transferred to and stored into any other computer connected to the image processing computer 30 and control computer 31 via a network.

Following the above procedure, first the image picked up by the ultraviolet CCD camera 33 is processed and analyzed to inspect the semiconductor wafer with a high resolution. If no defect can have been detected and classified using the ultraviolet light, or if the detected defect has a larger size than predetermined, the image picked up by the visible light CCD camera 32 is processed and analyzed to inspect the semiconductor wafer with a low resolution. Thus, a finer defect can be detected and classified than in the defect detection and classification using only the visible light. Further, if the defect detected using the ultraviolet light is large, the visible light is used to detect and classify the defect again. Therefore, even a relatively large defect can be classified with a high accuracy.

As having been described in the foregoing, the inspection equipment 1 according to the present invention detects a defect from reference and defect images picked up by the CCD cameras 32 and 33. This defect detection from the reference and defect images will further be described herebelow with reference to FIG. 12.

FIG. 12A shows an example of the image of a reference area in which a device pattern similar to a device pattern in a to-be-inspected area, namely, a reference image. FIG. 12B shows an example of the image of a to-be-inspected area in which a defect exists, namely, a defect image.

To detect a defect from such reference and defect images, the device pattern is extracted from the reference image based on color and gradation information, as shown in FIG. 12C. Also, an image of a difference between the reference and defect images is determined to extract as a defect a portion showing a large difference, as shown in FIG. 12D.

Then, the image of the extracted device pattern shown in FIG. 12C and image of the extracted defect shown in FIG. 12D are superposed on each other to provide a composite image as shown in FIG. 12E, from which a percent of defects in the device pattern, etc. are extracted as characteristics of the defect.

As having been described in the foregoing, the inspection equipment 1 inspects a semiconductor wafer for any defect by processing and analyzing, by means of the image processing computer 30, the reference and defect images picked up by the CCD cameras 32 and 33.

In the foregoing, there has been described the inspection equipment 1 used to examine what a defect on a semiconductor wafer is. However, the inspection equipment 1 is also used in any other applications than the discrimination of a defect in the semiconductor wafer. That is, the inspection equipment 1 is also usable to judge whether a device pattern formed in a semiconductor wafer has an appropriate shape reflecting precisely a desired pattern. Further, the application of the inspection equipment 1 is not limited to the inspection of a semiconductor wafer but it is widely applicable to inspection of fine patterns, for example, to inspection of a flat panel display having a fine pattern formed thereon.

What is claimed is:

1. An inspection equipment comprising:

means for supporting a specimen and moving the specimen to a predetermined position of inspection;

means for projecting an ultraviolet light through an ultraviolet objective lens onto the specimen supported on the specimen supporting means;

an ultraviolet imaging means for detecting a reflected or transmitted light from the specimen illuminated by the ultraviolet light projecting means to pick up an image of the specimen;

means for projecting a visible light to the specimen supported on the specimen supporting means;

visible light imaging means for detecting a reflected or transmitted light from the specimen illustrated by the visible light projecting means to pick up an image of the specimen;

means for processing the images picked up by the ultraviolet imaging means and the visible light imaging means selectively in response to the defect size of the specimen; and means for automatically selecting between the images picked up by ultraviolet imaging means and the visible light imaging means in response to the defect size of the specimen, the wavelength of the ultraviolet light emitted by the means for projecting an ultraviolet light, and the numerical aperture of the ultraviolet objective lens.

2. The equipment as set forth in claim 1, wherein the image picked up by the visible light imaging means is processed and analyzed by the image processing means to inspect the specimen with a low resolution; and the image picked up by the ultraviolet imaging means is processed and analyzed by the image processing means to inspect the specimen with a high resolution.

3. The equipment as set forth in claim 2, wherein the image picked up by the visible light imaging means is processed and analyzed by the image processing means to inspect the low frequency component, and the image picked up by the ultraviolet imaging means is processed and analyzed by the image processing means to inspect the high frequency component, thus dividing the band of a space frequency to be inspected.

4. The equipment as set forth in claim 2, wherein:

the visible light imaging means comprises a lamp as a light source to project an incoherent light from the light source to the specimen; and the ultraviolet imaging means comprises a laser as a light source to project a coherent light from the laser to the specimen.

5. The equipment as set forth in claim 1, wherein images of different areas of the specimen are picked up by the ultraviolet imaging means and the images are compared with each other by the image processing means to inspect the specimen.

6. The equipment as set forth in claim 1, further comprising:

a specimen placing mechanism for taking out the specimen having been carried in a predetermined container, from the container and placing it on the specimen supporting means; and a dedusting clean unit to keep clean the internal environment, wherein at least the specimen supporting means and specimen placing mechanism are provided inside the clean unit.

7. The equipment as set forth in claim 1, wherein the ultraviolet imaging means comprises an ultraviolet laser source as a light source to project an ultraviolet laser from the light source to the specimen.

8. The equipment as set forth in claim 7, wherein the ultraviolet laser source emits an ultraviolet laser having a wavelength of less than 355 nm.

9. The equipment as set forth in claim 7, wherein the ultraviolet laser source is a solid laser.

10. The equipment as set forth in claim 1, wherein the specimen is a semiconductor wafer having a predetermined device pattern formed therein.

11. The equipment as set forth in claim 1, wherein the defect size of the specimen is determined by the wavelength of the ultraviolet light emitted from the means for projecting ultraviolet light and the numerical aperture of the ultraviolet lens used in the projecting means.

12. The equipment as set forth in claim 11, wherein the image picked up by the visible light imaging means is processed and analyzed by the image processing means to inspect the low frequency component, and the image picked up by the ultraviolet imaging means is processed and analyzed by the image processing means to inspect the high frequency component, thus dividing the band of a space frequency to be inspected.

13. The equipment as set forth in claim 11, wherein the visible light imaging means comprises a lamp as a light source to project an incoherent light from the light source to the specimen and the ultraviolet imaging means comprises a laser as a light source to project a coherent light from the laser to the specimen.

14. The equipment as set forth in claim 11, wherein images of different areas of the specimen are picked up by the ultraviolet imaging means and are compared with each other by the image processing means to inspect the specimen.

15. The equipment as set forth in claim 11, further comprising:

a specimen placing mechanism for taking out the specimen having been carried in a predetermined container, from the container and placing it on the specimen supporting means; and a dedusting clean unit to keep clean the internal environment, wherein at least the specimen supporting means and specimen placing mechanism are provided inside the clean unit.

* * * * *